(12) United States Patent
Dutta

(10) Patent No.: US 9,851,353 B2
(45) Date of Patent: *Dec. 26, 2017

(54) HIGH SENSITIVITY MEDICAL DEVICE AND MANUFACTURING THEREOF

(71) Applicant: Banpil Photonics, Inc., Santa Clara, CA (US)

(72) Inventor: Achyut Dutta, Sunnyvale, CA (US)

(73) Assignee: Banpil Photonics, Inc., Santa Clara, CA (US)

( * ) Notice: Subject to any disclaimer, the term of this patent is extended or adjusted under 35 U.S.C. 154(b) by 1316 days.

This patent is subject to a terminal disclaimer.

(21) Appl. No.: 13/843,857

(22) Filed: Mar. 15, 2013

(65) Prior Publication Data
US 2014/0120603 A1  May 1, 2014
US 2017/0242008 A9  Aug. 24, 2017

Related U.S. Application Data

(60) Continuation-in-part of application No. 13/041,433, filed on Mar. 6, 2011, now Pat. No. 8,641,975, which is a division of application No. 11/552,080, filed on Oct. 23, 2006, now Pat. No. 7,922,976.

(51) Int. Cl.
*C12M 1/34* (2006.01)
*G01N 33/569* (2006.01)

(52) U.S. Cl.
CPC . *G01N 33/56988* (2013.01); *G01N 33/56983* (2013.01)

(58) Field of Classification Search
None
See application file for complete search history.

(56) References Cited

U.S. PATENT DOCUMENTS

| 7,768,650 | B2 * | 8/2010 | Bazylenko | G01N 21/253 356/491 |
| 7,922,976 | B2 * | 4/2011 | Dutta | B82Y 20/00 385/12 |
| 8,641,975 | B2 * | 2/2014 | Dutta | B82Y 20/00 385/12 |

* cited by examiner

*Primary Examiner* — Chris L Chin

(57) ABSTRACT

This invention relates to a system and methods including their manufacturing technologies for enhanced sensing capability of one or more bioagents covering from HIV, Pathogens, virus, to cells detection. More particularly, this invention is related to HIV and pathogen diagnosis system and methods which may increase its sensitivity and may reduce the diagnosis time. Furthermore, the diagnosis system and method may be applicable to all early stage patients with various age groups, where early and accuracy in diagnosis, are required.

10 Claims, 13 Drawing Sheets

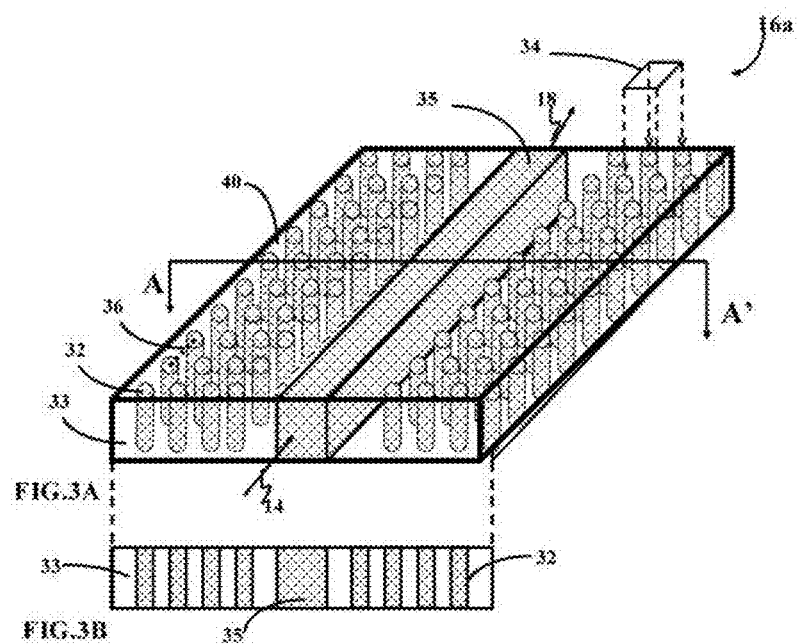
FIG.3A
FIG.3B
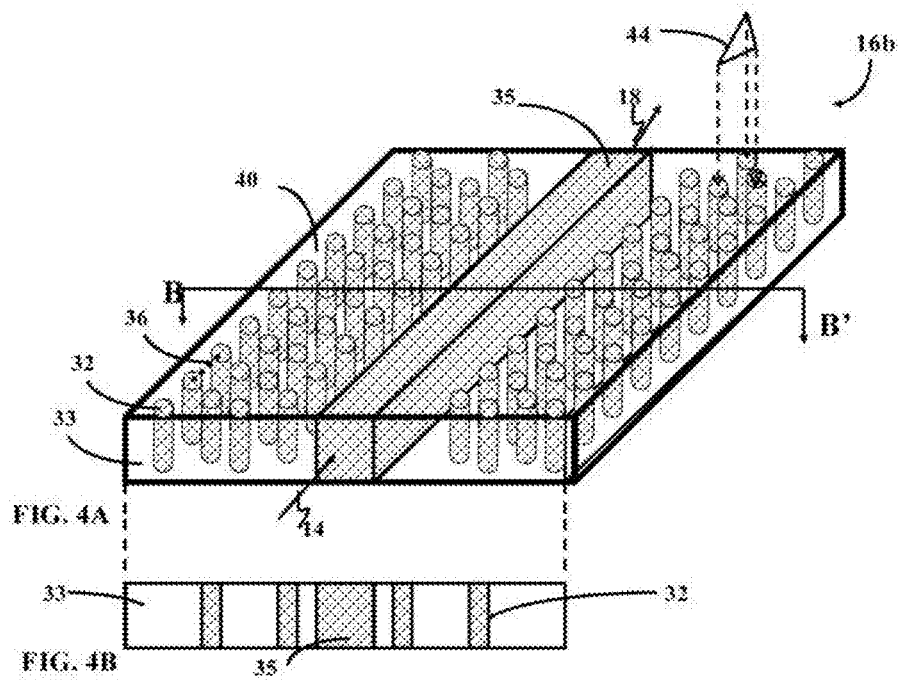
FIG. 4A
FIG. 4B

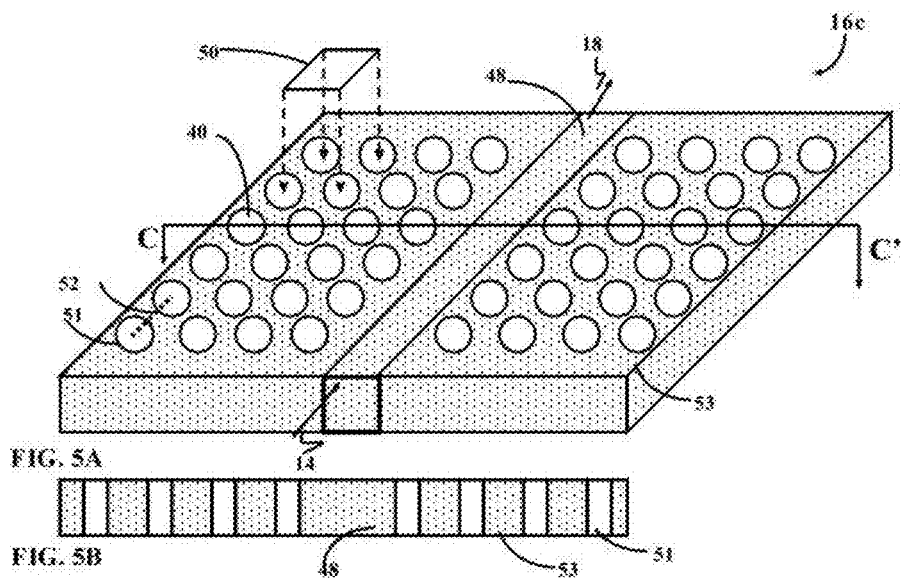
FIG. 5A
FIG. 5B
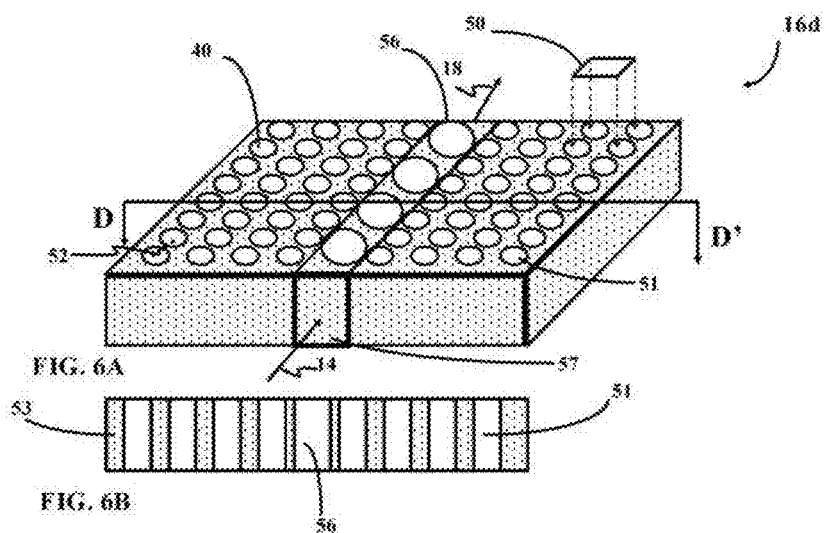
FIG. 6A
FIG. 6B

SEQUENCE LISTING

```
<160> NUMBER OF SEQ ID NOS: 2

<210> SEQ ID NO 1
<211> LENGTH: 19
<212> TYPE: RNA
<213> ORGANISM: Human immunodeficiency virus type 1

<400> SEQUENCE: 1
ucggucgauc gcuucauaa                                              19

<210> SEQ ID NO 2
<211> LENGTH: 16
<212> TYPE: RNA
```

```
<213> ORGANISM: Human immunodeficiency virus type 1

<400> SEQUENCE: 2
gaagcuugau cccgaa                                                          16
```

HIGH SENSITIVITY MEDICAL DEVICE AND MANUFACTURING THEREOF

This application is a continuation-in-part of U.S. patent application Ser. No. 13/041,433, filed on Mar. 6, 2011 (now U.S. Pat. No. 8,641,975), which is a divisional application of U.S. patent application Ser. No. 11/552,080, filed on Oct. 23, 2006 (now U.S. Pat. No. 7,922,976). This present application is also related to pending U.S. patent application Ser. No. 14/145,806, filed on Dec. 31, 2013, which is a divisional application of U.S. patent application Ser. No. 13/041,433, filed on Mar. 6, 2011 (now U.S. Pat. No. 8,641,975). This present application hereby claims the benefit of these earlier filing dates under 35 U.S.C. §120.

FIELD OF THE INVENTION

The present invention relates to high sensitivity sensor devices and its signal processing circuits to detect the gas, biomolecules, cells, or biochemical agents (altogether herein after mentioned as bio-agents). More specifically, this invention is related to sensor device comprising with at least one nano-chip for application in biomedical and industrial applications. Furthermore, the continuation in part is more particularly related to the system and method to diagnosis of virus, bacteria, cells, or infectious diseases, mainly found in body-fluidic system (e.g. fluid, blood) in human.

BACKGROUND OF THE INVENTION

The contents of all references, including articles, published patent applications and patents, if referred to anywhere in this specification are hereby incorporated by reference.

A large benefit of this sensor according to this invention, is that there can be several on a single wafer. It is a device able to measure chemical agent concentrations below part-per-billion (ppb) level and accurately determine the biomolecule agent and volume of biological cells present in human body. There is no device in the state-of-art, which allows concurrent detection of a chemical agent, biomolecule agent, and biological cell, all in a single system.

There are various kinds of sensor system. FIG. 1 shows a schematic representing the prior art of a sensor system 1 to detect biological cells, biomolecule agents or chemical agents (hereafter mentioned as specimen). The system 1 usually comprising with the sensor cell 2, power supply 4, detector 6, and analyzer 8. The system 1 usually detects or senses by detecting the electrical signal 10 induced due to absorption of the specimen. Detector 6 will detect the output signal 10 and send to the analyzer 8 to analyze the concentration of the specimen.

Several techniques can be found as the prior art for detecting concentration of specimen (common term used hereafter separately for chemical, biomolecule agents, or biological cells). However, most of them are based on the standard electrical technique wherein only single specimen is considered to detect. In addition, most technique requires long time in detection and/or not highly sensitive. The following, as a point of reference, are some methods, which are already patented and described as biosensors, used for detection of biological cells.

Peeters, in U.S. Pat. No. 6,325,904, (issued on Dec. 4, 2001), discloses a nanosensor, using an array of electrodes at the atomic or nano scale (nanoelectrodes) level, formed by using specific receptors. Utilizing the level of current flow while specific biological cells attached determine the concentration. The drawbacks of such technique are: (i) requiring STM to position the receptor which time consuming fabricating such sensor, (ii) requiring specific nano-scale level gap in between electrodes containing receptor to conduct current, (iii) difficulties in measuring low current level (corresponding to low concentration) due to use of computer controlled technique, and (iv) requiring high power due to using of computer controlled signal processing.

Bornhop, et al., in U.S. Pat. No. 6,809,828, (issued Oct. 26, 2004), discloses an sensor system for detecting proteins or DNA. Concentration is estimated based on the fringe pattern, detected by the CCD camera in addition with laser beam analyzer. Fringe pattern is usually depending on the laser intensity and position of the CCD camera. The drawback of this technique are, (i) in accuracy in concentration measurement as fringe pattern is dependent on the laser intensity and position, (ii) difficulties in low level concentration measurement due to difficulties in finding small changes in fringe pattern, and (iii) complete system becoming bulky as CCD camera, position sensor, and laser beam analyzer are to be used.

Britton, Jr., et al., in U.S. Pat. No. 6,167,748, (issued Jan. 2, 2001), discloses a technique for detecting the glucose concentration in blood. Measurement of concentration is performed based on standard technique of measuring the changes in capacitance. Technique uses cantilever coated with the receptor for absorbing the glucose. Main drawbacks are: (i) inability to detect low level concentration as very low changes in the capacitive is difficult to measure, and (ii) difficulties of detection of different kind of biological cell at the same time as each cantilever require different coating. Similar detection techniques can also be found in other patents such as U.S. Pat. No. 6,856,125, of Kermani (issued Feb. 15, 2005), U.S. Pat. No. 5,798,031 Charlton et al., (issued Aug. 25, 1998), U.S. Pat. No. 5,264,103 of Yoshioka et. al., (issued Nov. 23, 1993), and U.S. Pat. No. 5,120,420 of Nankai et. al., (issued Jun. 9, 1992), in all of which capacitive techniques are used to detect the concentration. Chemical and biological sensors can be miniaturized using nanowires or carbon nanotubes. Continued advances in nanoscience and nanotechnology require tiny sensors and devices to analyze small sample sizes. The following is a discussion of the prior art in sensor fabrication.

After discussing the above issues pertaining to the state-of-art biosensors, chemical sensors, and biomolecule sensors, and methods of making them, we would now like to introduce a novel technique where multiple chemical agents can concurrently be detected in real time and the information can quickly be transmitted to a main station and displayed. It is small in size, so the end user may carry it anywhere to measure the biological cell volume, protein, and biomolecule cells in a medical science application and is also able to do concurrent real time detection of different kinds of chemical agents.

Despite the advances in therapeutics and improved public health measures, infectious diseases still remain the major cause of morbidity and mortality in most parts of the world. Clinical syndromes are rarely specific for single pathogens, so multiplexed diagnostics provide good detection sensitivity, but are often slow, bulky, expensive, and reliant on trained medical personnel. The development of handheld diagnostic systems that can provide rapid diagnosis for multiplexed detection of pathogens could significantly contribute to the prevention and treatment of infectious diseases.

Similarly, that same multiplexed detection technology can be utilized to diagnose a single condition, such as HIV. Studies have shown that people newly infected with HIV are most contagious because of the initial high viral loads. However, early stage detection is currently expensive and inaccurate. These detection systems have proven to be of limited benefit. Many potentially infected people cannot afford the laboratory testing necessary, or cannot justify the cost due to the chances of a misdiagnosis. The multiplexed sensor described herein, however, will be relatively inexpensive, can be used by the average consumer, and will give results quickly and accurately. There is thus a corresponding need to develop a universal diagnosis device, which can diagnosis multiple bio-agents (including infectious diseases, cells, DNA, RNA etc.), improve the effectiveness, sensitivity, and accuracy of diagnosis by reducing time and complexity, and by improving accuracy and consistency of assessment of diagnosis studies. There is a clear role and need for a system and methods, to improve sensitivity, accuracy, and diagnosis time and facilitate more accurate and consistent diagnosis.

SUMMARY OF THE INVENTION

According to this current invention, it is an object to provide a sensor system comprising with a sensor more specifically relates to a novel nano-sensor. It is also object to provide the embodiments including novel methods, systems, devices, and apparatus for sensing one or more characteristics. One aspect of the present invention is a sensor, which is capable of distinguishing between different molecular structures in chemical agents at the same time. It is also capable of distinguishing between different types of biomolecule agents or biological cell concentrations. It is capable of detecting the concentration of different types of chemical agents, biomolecule agents, and biological cells.

This present sensor system is based on any type waveguide, including but not limited to: the slab waveguide, the ridge waveguide, or a dielectric materials structure based waveguide. Its bottom clad (hereafter mentioned as substrate) can be formed using an array of various dielectric materials, structured periodically, which can form the photonic-band-gap (PBG). In waveguide, the guided light usually suffers radiation loss due to weak optical confinement; this happens when the structure is not well optimized or the structural parameters are interrupted. The sensor structure is optimized for a fixed wavelength and is designed in such a way that the propagation loss is minimal. Alternatively, according to this invention, the sensor can also be designed to operate in broadband light operation. In that case, the waveguide for nano-chip can be designed to operate multi-mode of operation.

This sensor detects the concentration of gases (that exist in air) based on the change in the effective refractive index of the substrate caused when biomolecule gas/chemical agents fill the air (or receptor) spaces. The changes in the effective refractive index reduce the output optical power (measurable parameter). By comparing the output optical power with the reference input optical power, the proposed nanosensor can detect the biomolecule gas/chemical agent concentration in ppb levels.

It is noted here that the type of chemical agent/gas can be specified by using a fixed receptor specifically made for absorbing said agent/gas. Also, the type of biomolecule agent or biological cell can be specified by using a fixed receptor to absorb the said biomolecule agent or biological cell. The concentration of the agent/gas and the biomolecule agent, and the volume of biological cells can be ascertained by measuring the output optical power, which is a function of the change in effective refractive index and density. In this case, the detector will detect the presence of a chemical agent/gas or a biomolecule agent or a biological cell. Then it will generate an electrical signal, which will be processed through a processing circuit. After the processing circuit, a digital monitoring system will display the actual concentration present via LED.

The materials used for the nanosensor and surrounding surfaces are selected based on their electrical and chemical properties. The PBG arrays may be included in a chamber, which can retain fluid for biological applications; another set of arrays can be used for chemical agents/gas detection. Several arrays may be used in a single chamber and several different chambers may be used in a single chip. Thus, one system may detect chemical agents/gas, biomolecule agents, and biological cells.

This proposed PBG based nanosensor array and chamber as attached should be separated from each other on a chip, so that each system works properly for each individual application. A Digital Signal Processing (DSP) function, Analog to Digital Converter (ADC), and microprocessor are provided to analyze signals from the nanosensors and/or do real time calculations of the accurate values obtained from the nanosensor.

In some other embodiments a communication setup is used in order to relay the output values long distances. This communication setup is included to analyze the real time sensing values remotely.

Further embodiments, forms, features, objects and advantages of the present invention will be apparent from the following description.

Further, two specific embodiments for medical application are included. First, described is an embodiment for detecting pathogens, such as Hepatitis B (HBV), through testing of blood, saliva, or other body tissue. Second, described is an embodiment for detecting HIV in the blood.

BRIEF DESCRIPTION OF THE DRAWINGS

The features and advantages of the present invention will become apparent and may be better understood from the following detailed description of the system, taken in conjunction with the accompanying drawings, wherein

FIG. 3A is a enlarged view of a nano-chip comprising with a waveguide based on photonic bandgap (or photonic crystal) structures having rectangular lattice, according to this invention, and FIG. 3B is a cross-section view across AA' as shown in FIG. 3A.

FIG. 4 is a schematic diagram of a nano-chip comprising with a waveguide based on photonic bandgap (or photonic crystal) structures having triangular lattice according to this invention, and FIG. 4B is a cross-section view across BB' as shown in FIG. 4A.

FIG. 5 is a schematic diagram of a nano-chip comprising with a waveguide based on photonic bandgap (or photonic crystal) structures having rectangular lattice, according to this invention, and FIG. 5B is a cross-section view across CC' as shown in FIG. 5A, where the PBG is rectangular in shape with holes and a slab waveguide is used.

FIG. 6 is a schematic diagram of a nano-chip comprising with a waveguide based on photonic bandgap (or photonic crystal) structures having defects and rectangular lattice, according to this invention, and FIG. 6B is a cross-section view across DD' as shown in FIG. 6A.

FIGS. 10B and 10C are output signals at points A and B, shown in FIG. 10A.

FIGS. 11B and 11C are output signals showing with capture points, with and without specimen absorption.

DETAILED DESCRIPTION OF THE PREFERRED EMBODIMENT

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention.

In the following detailed description of the preferred embodiments, reference is made to the accompanying drawings, which form a part hereof, and in which is shown by way of illustration specific preferred embodiments in which the inventions may be practiced. These embodiments are described in sufficient detail to enable those skilled in the art to practice the invention and it is to be understood that other embodiments may be utilized. The following detailed description is, therefore, not to be taken in a limiting sense, and the scope of the present invention is defined only by the appended claims.

According to this current invention, it is our objective to provide a sensing device comprising with nano-sensor and its signal processing circuit which can have the significantly high sensitivity. The sensor device detects the specimen concentration based on the principle of optics. Using of the nano-sensor and signal processing circuit, according to this invention, high sensitivity can be achieved. Detection is mainly based on detecting the difference in intensity of optical signal obtained after specimen absorb in the receptor and converting to electrical signal and their arithmetic processing to achieve significant high sensitivity.

Figure 1:
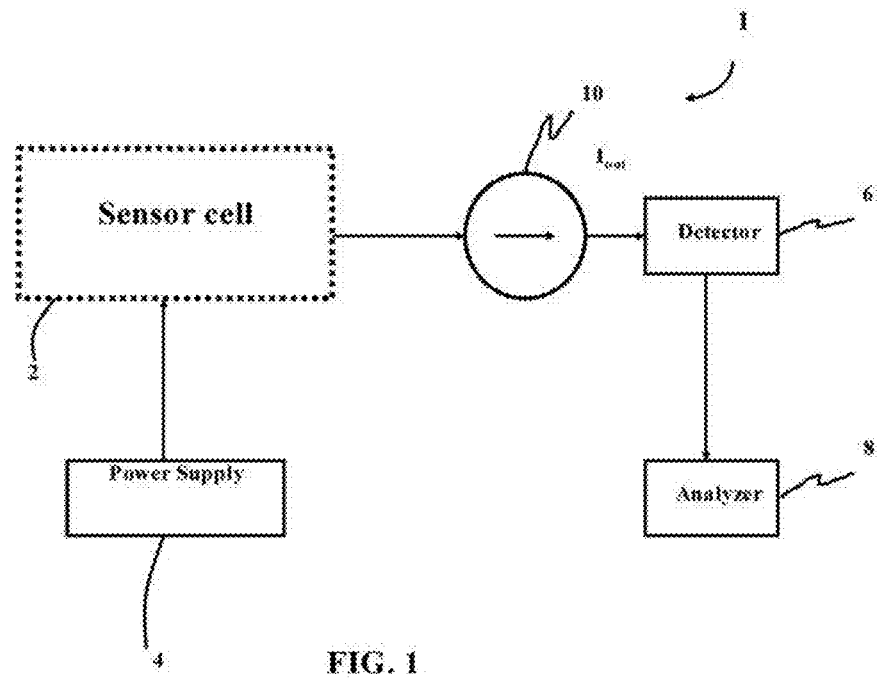
FIG. 1 is a schematic of sensor system in prior art.
Figure 2:
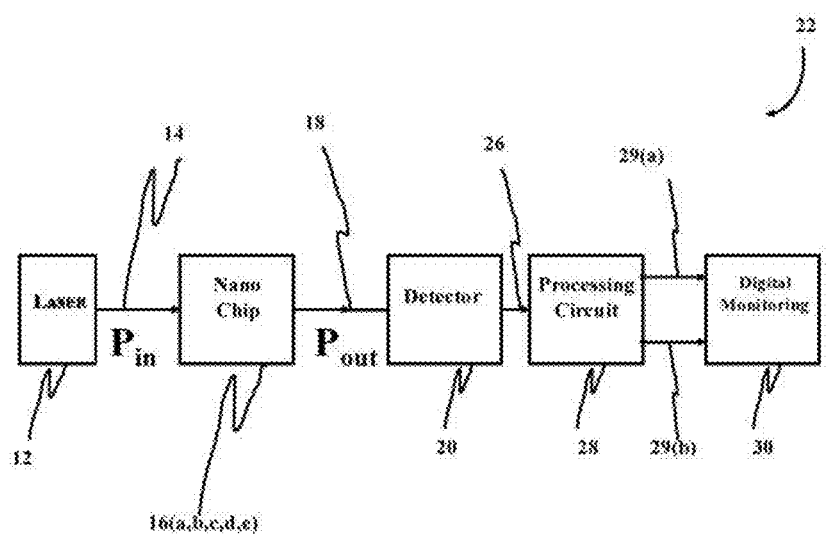
FIG. 2 are the block diagrams representing the schematic of the sensor system for detecting the gas, bio-molecule, or biological cell concentration.

FIG. 2 shows a block diagram of the system according to this invention. In block diagram 22, input optical signal 14 is generated from a laser 12 having a wavelength ranging from ultra-violet to infrared. The signal 14 will pass through the nano-chip 16(a, b, c, d, e). For a unique and optimized design (with no presence of specimen or sample) intensity of output optical power 18 from the nano-chip 16(a, b, c, d, e) can be same as that of input optical power 14. This means that the coupling loss though the nano-chip is be zero. The presence of the specimen or sample inside of the nano-chip 16(a, b, c, d, e) will cause a reduction in the output optical power 18, detected by the detector 20. The reduction in output optical power 18, if any, is due to the change in the refractive index of the receptors with and without absorption of the specimen. The receptor is usually contained in the nano-chip 16(a, b, c, d, e), explained later in FIG. 3. The detector 20 is used to convert the optical signal 18 into an electrical signal 26 and the said electrical signal 26 is processed through the processing circuit 28, explained later in detail in FIGS. 9-13. The resultant signals 29(a) and 29(b) from said processing circuit 28 is passed through digital signal processing circuit (DSP) 30 where related arithmetic function can be performed to monitor actual concentration of the specimen in real time. Details of the DSP circuits are provided in FIG. 13.

According to this invention, the processing circuit can be made in hybrid using different functional chips or using single chip having all functions, and those can be fabricated from 350 nm or less geometry. The detector can be chosen based on the wavelength of the light to be used in the system 22. For example, if the wavelength is selected in visible region, the silicon-detector can be used in system 22. On the other hands, if the wavelength of near infrared is chosen, then the detector made from III-V compound semiconductor is required for having higher sensitivity.

According to this invention, the system 22 can be miniaturized into a very small package (e.g. less than 1 to 0.5 inches in dimension). The main advantage of the system 22, according to this invention, is that only the power of output optical signal 18 needs to be known in order to ascertain the concentration. In system 22, very little power will be absorbed by the nano-chip and this is based on the percentage of the refractive index change. The system 22 has two parts: the first is a 'detection part' comprising of laser 12, nano-chip 16(a, b, c, d, e), and the detector 20; the second is an 'analyzing part', comprising of signal processing circuits 28 and 30.

According to this invention, different nano-chips 16(a, b, c, d, e) are explained in FIGS. 3 to 7. FIG. 3A shows a schematic, representing the enlarge view of a nano-chip 16a and FIG. 3B is the cross-sectional view of section AA', as shown in FIG. 3A. According to this invention, the nano-chip 16a can be made from photonic crystal comprising of dielectric rods 32 arranged periodically in hollow clad 33 (hereafter we define clad as a substrate with a refractive index '$n_{sub}$') to form a photonic-band-gap (PBG) and/or photonics-crystal structures, having rectangular lattice 34. The nano-chip 16a has waveguide structure having core 35 having refractive index of '$n_{core}$'. Each rod 32 has a radius of 'r' (from 0.1 μm to 0.3 μm or may be in different size depending on the design) and they are separated by a distance 'a' (known as pitch or lattice constant) 36, which is equal to or greater than '2r'. Receptors 40 can be placed in-between the spaces of the rods 32 in hollow clad 33.

Receptors 40, shown in FIG. 3 (For example: ACh—Acetylcholine covers for nerve agents, AH—Aromatic Hydrocarbon, etc.) can be used inside the nano-chip 16(a, b, c, d, e). Here, receptor 40 is used to detect the type of specimen and they absorb/interact with the respective specimen (e.g. biomolecule or chemical agents or biological cell) present in between the spaces of the dielectric rods.

Each rod 32 has a refractive index 'n' which can be either equal to '$n_{core}$' or refractive index 'n' can be greater or less than the core refractive index $n_{core}$'. Optical signal input 14 to nano-chip 16a is transmitted through the core 35. Based on the absorption of the specimen (not shown here) by the receptor 40 located in the space between the rods 32, the refractive index of the substrate '$n_{sub}$' in combination with hollow clad 33 and receptor 40 is changed to '$n_{eff}$', the effective refractive index, and as a result, the power output optical signal 18 is reduced. The concentration of the specimen can be determined by calculating the change of the refractive index of the receptors 40 after and before of absorption of the specimen and the changes in power of the optical signal 18 with respect to input optical signal 14. Changes in power of optical signals between 14 and 18 can be determined by the power-factor, which is defined as the ratio of the output optical power over the input optical power. According to this invention, the main advantage is that by knowing the power factor, the changes in refractive index and also the concentration of the specimen can be determined. By calculating the power-factor, this proposed sensor would give the real-time concentration of the specimen.

Nano-chip 16a used for system 22 is based on photonic-crystal and they are having different structures. Two-dimensional (2-D) or three-dimensional (3-D) photonic crystal can be used to fabricate the nano-chip 16a. In FIG. 3A, the photonic crystal is formed based on the dielectric rods 32. Alternatively, the photonic crystal can be also made from holes, periodically arranged inside the dielectric materials.

FIG. 4A shows a schematic, representing the enlarge view of an alternative nano-chip 16b and FIG. 4B is the cross-sectional view of section BB', as shown in FIG. 4A, according to this invention wherein the same numerals in FIGS. 4A and 4B represent the same parts in FIGS. 3A and 3B, so that repeated explanation is omitted here. Only difference in FIGS. 4A and 4B as compared with FIGS. 3A and 3B is that the photonic crystal is made from the dielectric rods 32 placed in hollow clad 33, wherein the rods 32 is having the triangular lattice 44.

FIG. 5A shows a schematic, representing the enlarge view of an alternative nano-chip 16c and FIG. 5B is the cross-sectional view of section CC', as shown in FIG. 5A, according to this invention, wherein the same numerals in FIGS. 5A and 5B represent the same parts in FIGS. 3A, 3B 4A, and 4B, so that repeated explanation is omitted here. The main difference in FIGS. 5A and 5B as compared with FIGS. 3A, 3B, 4A, and 4B is that the photonic crystal is based on the holes 51 periodically arranged inside the slab acting as the clad 53, wherein the holes 51 are filled up with the receptors 40 and also the holes 51 is having the rectangular shaped lattice 50. According to this invention, optical signal 14 is guided through the slab-type waveguide 48 located inside slab (or clad) 53. Each hole 51 in nano-chip 16c has a radius of 'r' and they are separated by a distance 'a' (also known as lattice constant) 52. Inside each hole, receptors 40 are present to absorb/interact with the specimen/sample. 54 shows the cross sectional view of this nano-chip 16c. The nano-chip can also be designed by making holes in a triangular shape. Specification of the radii of the holes 'r' and lattice constant 'a' 52 will be optimized depending on the size of the nano-chip 16c.

FIG. 6A shows a schematic, representing the enlarge view of an alternative nano-chip 16d and FIG. 6B is the cross-sectional view of section DD', as shown in FIG. 6A, according to this invention, wherein the same numerals in FIGS. 6A and 6B represent the same parts in FIGS. 3A, 3B 4A, 4B, 5A, and 5B, so that repeated explanation is omitted here. The main difference in FIGS. 6A and 6B as compared with FIGS. 5A and 5B is that the nano-chip 16d is also based on photonic crystal, but comprising with defects 56 in the holes periodically structure in the core 57. "Defects in the holes," means that the diameter of some holes is bigger than the diameter of the 'regular' holes, all structured periodically. According to this invention, the defects 56 can also be filled with the receptor 40 and they can be created either using of holes 56, as shown in FIGS. 6A and 6B, or using of the solid rods having specific radius (not shown here).

Figure 7:
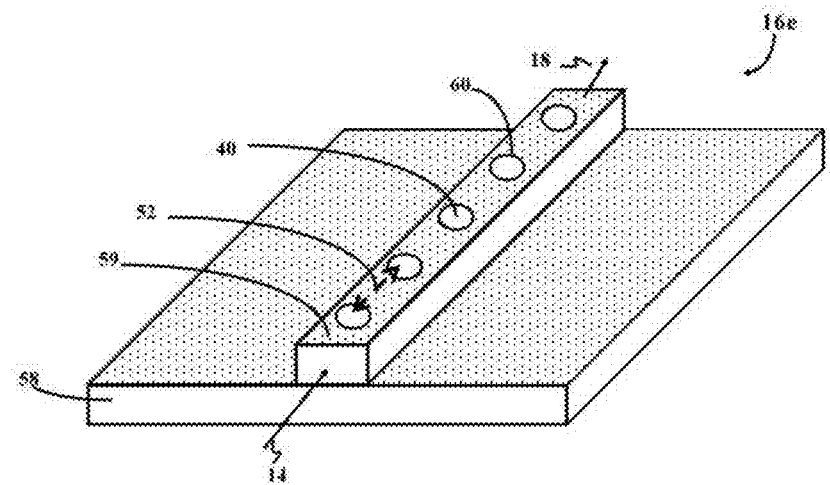
FIG. 7 is a schematic diagram of a nano-chip comprising with a waveguide based on photonic bandgap (or photonic crystal) structures having defects, according to this invention.

FIG. 7 shows a schematic, representing the enlarge view of an alternative nano-chip 16e, according to this invention, wherein the same numerals in FIG. 7 represent the same parts in FIGS. 6A and 6B, so that repeated explanation is omitted here. The main difference in FIG. 7 as compared with FIGS. 6A and 6B is that the nano-chip 16e is based on the solid slab 58 acting as the clad and the core 59 to guide the optical signal 14, comprises with holes as defects 60 arranged periodically inside core 59 forming photonic band gap structure. As mentioned earlier, any type of specimen can be detected and their concentration can be known after processing the output optical signal 18 from nanochip. Type and concentration of any specimen such as gases, biomolecules, or any biological cells can be detected by making them to absorb on corresponding receptor 40 to be used in the holes 60.

The nano-chip 16(a, b, c, d, and e), can be fabricated using dielectrics, semiconductor, or polymer materials. The dielectric material can cover all kind of materials having dielectric or optical properties (e.g. refractive index), such as glass, quartz, polymer etc. According to this invention, alternatively, the nano-chip can also be fabricated from semiconductor materials, such as Si, GaAs, InP, GaN, SiC, diamond, graphite etc. which can be fabricated using standard's IC fabrication technology. This nano-chip itself can be from rigid or flexible substrate.

The nano-chip can be fabricated by standard dry or wet etching to form the holes or rods embedded inside the solid or hollow substrate. Alternatively, this can also be fabricated using spin-coated polymer or preformed polymer. The low shrinkage in polymerization and the transparency of the synthesized polyurethane can also be used in fabrication of infiltrated inverse opal elastomeric photonic-crystal structures for the nano-chip according to this invention. The nano-chip 16(a, b, c, d, and e) can have high-symmetry cross-sections and can allow integrated optical networks to be formed by only placing either the rods in air or air cylinders in the dielectric. The nano-chip 16 can also be fabricated in multiple layers by stacking the slabs on top of one another, separating them with a separator. According to this invention, the nano-chip 16(a, b, c, d, and e) and surrounding circuitry can be made into the single chips using today's IC process technology.

The specific specimen can be detected using the nanochip with specific receptor. For example, Avidin Biotin which is the most common uses as a receptor for glycoconjugate analysis and DNA detection systems, can be used also as the receptor 40 in the nanochip 16(a,b,c,d, and e). Single receptor agent or solution linked with other molecule acting as the receptor (for the specific specimen) can also be used as receptor 40. For example, Dimethylsulfoxide (DMSO) solution containing 4 mg/ml of the heterobifunctional linker molecule succinimidyl-6-hexanoate (biotinamido) for a 1 hour at room temperature and the resultant receptor can be used as receptor 40 for DNA detection. According to this invention, the receptor 40 can be gel-type, solid, or solution based.

A derivation is given here for the generalized analytical equation for the nanochip described earlier in FIGS. 3 to 7. This derivation helps to understand the insight of this current invention for high sensitivity sensor device. For simplicity in derivation, nano-chip, as shown in FIG. 7, consisting of a ridge waveguide in the core formed by periodically structured PBG, is considered as the example and this nanochip can be considered as a linear system. The waveguide structure is considered to be optimized for providing almost same output optical power 18 for the specific wavelength of the optical input 14. By knowing the output optical power the concentration of the specimen (e.g. biological cells, industrial gas, or biological cell agents) can be detected. According to this current invention, nano-chip is considered to be formed based on the 2-D photonic crystals. Related generalized equations, required for determining specimen concentration is described herewith. Noted here that type of specimen can be known from the specific receptor 40, as explained earlier. The specific receptor is used for specific link or bond.

According to this invention, the waveguide structure is to be designed in such a way that maximum optical power for optical signal 18 is achieved (or very to optical power of input optical signal 14), and that condition (or optical power) can be considered as the reference (i.e. with specimen present) in the holes. The symbol used in derivation is summarized in Table I.

TABLE I

Description of the symbols used in derivation

| Parameter | Description |
|---|---|
| $n_{cref}$ | Reference refractive index of the core |
| $n_{ceff}$ | Effective (new) refractive index of the core |
| N | Gladstone-Dale constant |
| $P_{in}$ | Input optical Power |
| $P_{out}$ | Output Optical Power |
| Power Factor = $P_{out}/P_{in}$ | Ratio of output optical power and input optical power |
| $\rho_{ref}$ | Reference density (air or filled with receptor) |
| $\rho_{new}$ | New density after specimen absorbed |
| $\Delta_\rho$ | Change in density |

For linear system with ridge waveguide, Power Factor, ratio of output optical power ($P_{out}$) to input optical power can be derived as follows:

$$\text{Power Factor} = \frac{P_{out}}{P_{in}} = 1 - \frac{n_{cref}^2 - n_{ceff}^2}{n_{cref}^2 - n_{clad}^2} \quad (1a)$$

Where, $n_{cref}$ is the reference refractive index of the core with optimized waveguide. $n_{ceff}$ is the effective refractive index of the core and $n_{clad}$ is the refractive index of the clad. From Eq. (1a), coupling loss can be written as $$\text{Coupling Loss} = 1 - \text{Power Factor} \quad (1b)$$

Where, Coupling Loss is, $$\text{Coupling Loss} = \frac{n_{cref}^2 - n_{ceff}^2}{n_{cref}^2 - n_{clad}^2} \quad (1c)$$

From Eq. (1a), relationship between Power Factor and density of the gas can be derived. The relationship between $n_{cref}$, reference core refractive index (with no gas condition) and $\rho_{ref}$, reference density of receptor can be expressed by using of Gladstone-Dale relationship, $$n_{cref} - 1 = \rho_{ref} \times N \quad (2)$$

where, N is the Gladstone-Dale constant

As mentioned earlier, after sensing the gas, the density of the receptor $\rho_{new}$, after absorbing the gas which changes the effective refractive index of the substrate, nceff (mentioned as new core effective refractive index). Similarly, nceff relates with $\rho_{new}$ as, $$n_{ceff} - 1 = \rho_{new} \times N \quad (3)$$

From Eqs. (2) and (3), this following expression can be derived:

$$\frac{n_{cref} - 1}{n_{ceff} - 1} = \frac{\rho_{ref} XN}{\rho_{eff} XN} \quad (4)$$

From Eq. (4) $n_{ceff}$ expression can be derived as:

$$n_{ceff} = 1 + \frac{(n_{cref} - 1)}{\rho_{ref}} \rho_{new} \quad (5a)$$

After substituting Eq. (5a) into Eq. (1a), we get the new density as follows:

$$\rho_{new} = \frac{\left[\sqrt{n_{cref}^2 - (1 - \text{Power Factor})(n_{cref}^2 - n_{clad}^2)} - 1\right]\rho_{ref}}{(n_{cref} - 1)} \quad (5b)$$

Changes in density $\rho$ can be expressed as, $$\Delta\rho = \rho_{new} - \rho_{ref} \quad (6)$$

Concentration of the bio-agent in ppb, which is a function of the molecular weight and $\Delta\rho$, and ppb can be written as $$ppb = \frac{\Delta\rho \times 0.02}{\text{Molecular Weight}} \quad (7)$$

After substituting Eq. (6) into Eq. (7), the concentration of gas in ppb can be expressed as:

$$ppb = (\rho_{new} - \rho_{ref})\frac{0.02}{\text{Molecular Weight}} \qquad (8)$$

Now substitute value of $\rho_{new}$ in Eq. (8) and we can derive ppb, which is $$ppb = \left[\frac{[\sqrt{n_{cref}^2 - (1-\text{Power Factor})(n_{cref}^2 - n_{clad}^2)} - 1]\rho_{ref}}{(n_{cref}-1)} - \rho_{ref}\right] \times \frac{0.02}{\text{Molecular Weight}} \qquad (9)$$

Alternatively, particularly for medical diagnosis purposes, the above calculations can instead be done to allow for sensing target biomolecules in a non-gaseous form, and at even lower concentrations, such as parts per billion (ppb).

$$ppb = \left[\frac{[\sqrt{n_{cref}^2 - (1-\text{Power Factor})(n_{cref}^2 - n_{clad}^2)} - 1]\rho_{ref}}{(n_{cref}-1)} - \rho_{ref}\right] \times \frac{(0.02)}{\text{Molecular Weight}} \qquad (10)$$

Potentially, biomolecules might be detectable in ppb or even further lower concentrations, such as parts per trillion or even quadrillion.

Figure 14:
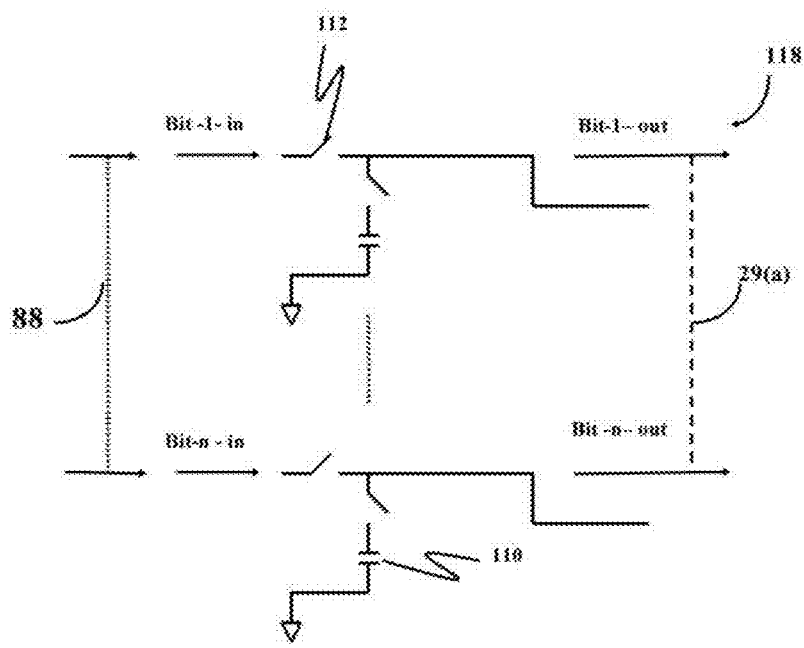
FIG. 14 is a schematic representing an alternative read-out circuit to store the reference signal.
Figure 15:
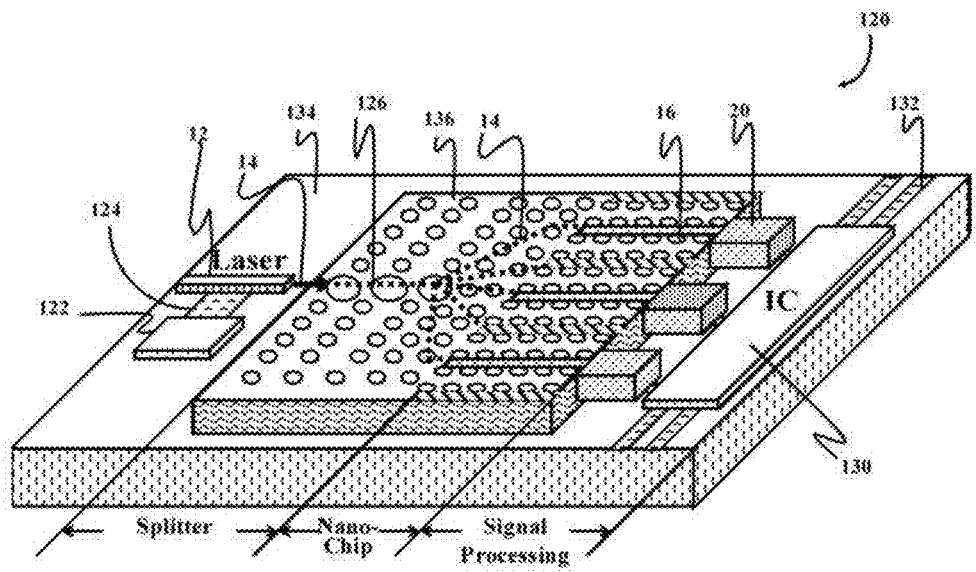
FIG. 15 is a schematic showing an example of a complete sensor device for multiple specimens' detection, according to this invention.
Figure 16:
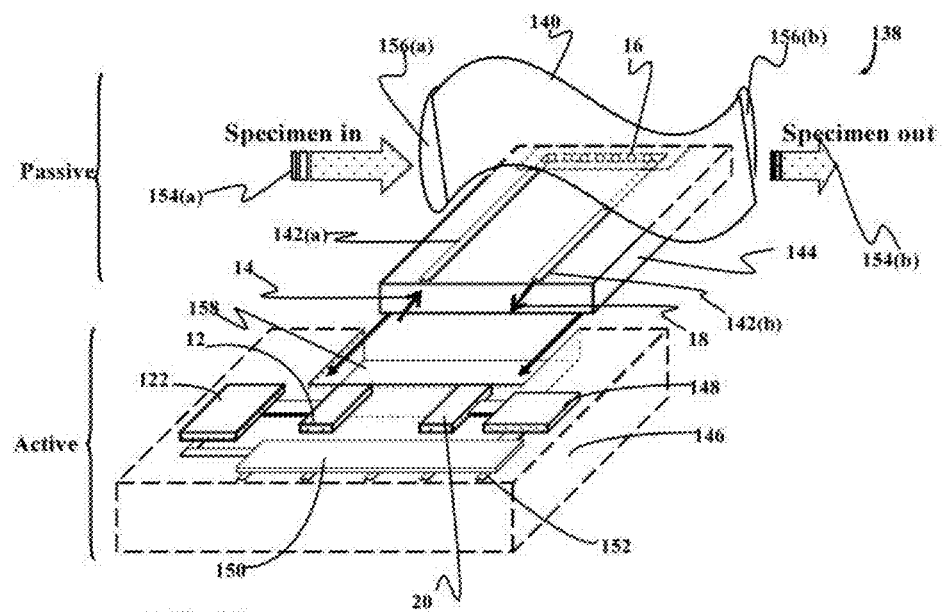
FIG. 16 is a schematic showing an example of a complete sensor device, packaged in small form-factor, according to this invention.

According to this invention, by knowing the power factor (which is ratio of power of optical out 18 to power of optical in 12 to and from the nanochip 16, respectively to the optical input), and appropriate arithmetic signal processing, the concentration of the specimen can be known. According to this invention, the gas is considered, it can be also be used for biomolecule gas, or biomolecule cells, if corresponding receptor is used. From FIGS. 8 to 14, the signal processing for detecting small change in power factor are given. FIGS. 15 and 16 explain the sensor device according to this invention.

Figure 8:
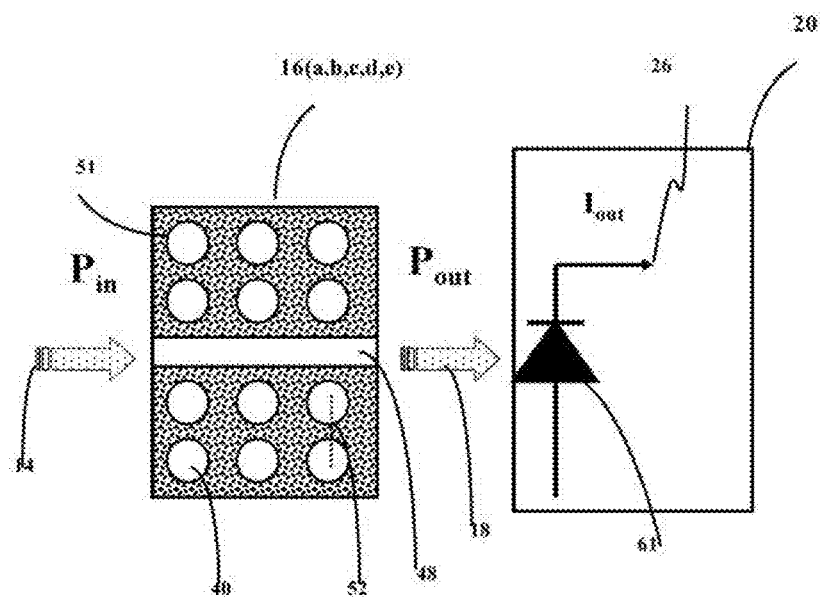
FIG. 8 is schematic of interconnection between the nano-chip and its detector.

FIG. 8 shows a schematic representing the nano-chip and its detection block diagram according to this invention wherein same numerals represents the similar parts shown in FIGS. 2, 3, 4, 5, 6, and 7, so that similar explanation is omitted here. In FIG. 8, the optical signal 18 from nano-chip 16(*a, b, c, d,* or *e*) is detected by the (optical) detector 61 to convert into corresponding electrical signal 26. The detector 61 should be selected based on the wavelength of the light used in the nano-chip. For example, for visible wavelength, Si-based photodetector can be used which can provide quantum efficiency close to 100% over visible wavelength. For Near infrared wavelength, III-V compound semiconductor based detector can be used.

Photodiodes can be used in either zero bias or reverse bias. In zero bias, light falling on the diode causes a voltage to develop across the device, which leads to current flowing in the forward bias direction. Diodes usually have extremely high resistance when reverse biased. This resistance is reduced when light of an appropriate wavelength incident onto the junction. Hence, a reverse biased diode can be used to generate the photo current. Circuit with reverse-biased detector is more sensitive to light than one with zero-biased detector.

The detector can be p-n junction based detector or avalanche photodiode (APD) detector, According to this invention; both type photodetector (p-n or APD) can be used. Only difference is there operational voltage. For example, APD requires high voltage and on the other hands, p-n junction requires low voltage. By using of APD, according to this invention, single photon level difference in optical power between input to nano-chip and output from nano-chip can be detected.

Figure 9:
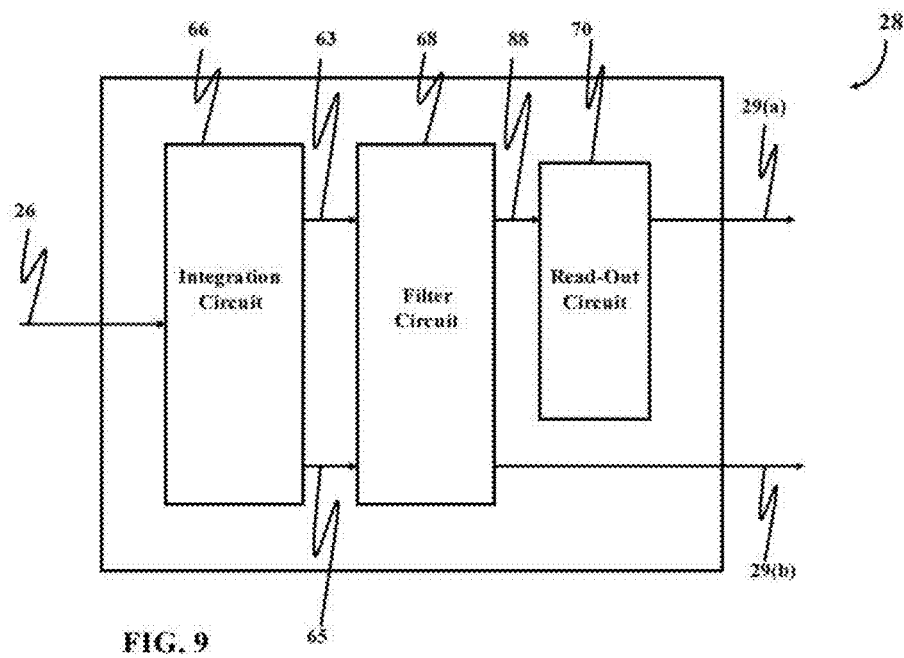
FIG. 9 is the block diagram representing an example of an electrical signal processing circuit to detect the specimen, according to this invention.

FIG. 9 shows the signal processing block diagrams according to this invention wherein same numerals represents the similar parts shown in FIG. 8, so that similar explanation is omitted here. According to this invention, Electrical-processing circuit 28, shown in FIG. 9, comprises with electrical signal integration circuit 66, filtering and sample-counter circuit 68 to remove electrical noise, and a read-out circuit 70 to store the data. Each of these blocks 66, 68, and 70 are explained in details in FIGS. 10, 11, and 12. The electrical signal outputs from this signal-processing unit 28 are reference signal 29(*a*) and signal 29(*b*) after specimen absorbed by the nano-chip. In absence of specimen absorption, the electrical signals 29(*a*) and 29(*b*) are the same.

Figure 10A:
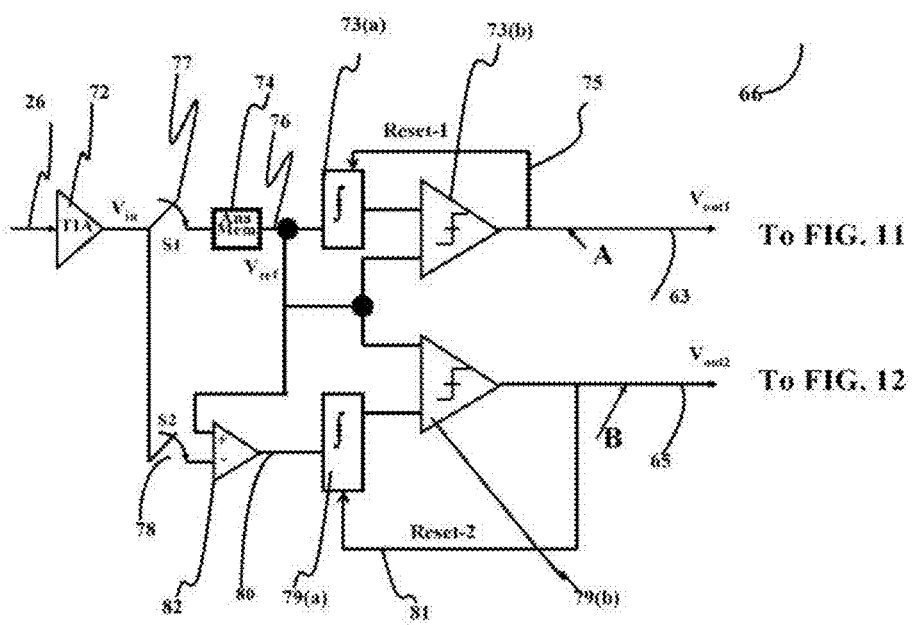
FIG. 10A is a schematic representing a integration circuit unit for signal pre-processing, a part of processing circuit, as shown in FIG. 9, according to this invention.

FIG. 10A shows the integrated circuit block in details, of the block diagrams, as shown in FIG. 9, and FIGS. 10B and 10C are the waveforms of point A and B, as shown in FIG. 10A, according to this invention wherein same numerals represent the similar parts shown in FIGS. 8 and 9, so that similar explanation is omitted here. The electrical integration circuit 66 means as shown in FIG. 10 is a part of the electrical processing circuits 28. According to this invention, electrical integration circuit 66 means comprises with transimpedance amplifier (TIA) 72, two sets of switches 77 and 78, a an analog memory 74 to store the reference value as reference voltage 76, and two sets of integrator circuits 73(*a*) and 79(*a*), two sets of comparators 73(*b*) and 79(*b*), and one differentiator 82.

According to this invention, the signal 26 input to TIA 72 of the integrated circuit 66 to have the proportional voltage output $V_{in}$. Initially, the switch S1 77 is on and switch S2 78 is off. While the Switch S1 77 is on, the proportional voltage output $V_{in}$ is directly feed through the analog memory 74 to store the initial voltage as the reference voltage 76 (output of analog memory 74). Noted here that the reference voltage $V_{ref}$ can be either same or greater than that the proportional voltage output $V_{in}$. The reference voltage $V_{ref}$ is integrated by the integrator 73(*a*) and its output is directly feed to the comparator 73(*b*) whose other input is set to $V_{ref}$. While the integrator 73(*a*) output is reached to $V_{ref}$, the comparator 73(*b*) output will reset the Integrator 73(*a*). The resultant waveform 63 from comparator 73(*b*) is saw-tooth type waveforms as shown in FIG. 10B for the point A of FIG. 10A. The resultant waveform 63 is acted as the output of $V_{ref}$ and mentioned here as $V_{out1}$, while there is no absorption of the specimen in the nano-chip explained earlier. As soon as integration for the pre-desired cycle (explained later in FIG. 10B) is completed, the switch S1 77 is turned to OFF and at the same time S2 78 is turned on and the output from the TIA 72 is directly feed to the differentiator 82 whose other input is output 76 from Analog memory 74. The differences 80, output from the differentiator 82 is similarly feed to the integrator 79(*a*), whose output is again feed to the comparator 79(*b*). Noted here that other input to the comparator 79(*b*) is $V_{ref}$. The resultant waveform 65 is also saw-tooth like waveform (mentioned as $V_{out2}$), as shown in FIG. 10C

(at point B) and it can be generated by the reset 81, as mentioned earlier. The differences between two sets of circuits as shown in FIG. 10A after and before switch S1 77 ON and OFF is that they process the signals without and specimen absorption, respectively. According to this invention, the output waveforms 63 and 65 comprises with stream of saw-tooth like waveforms 83(a) and 83(b) which can be processed for captured explained later in FIG. 12.

Figure 11A:
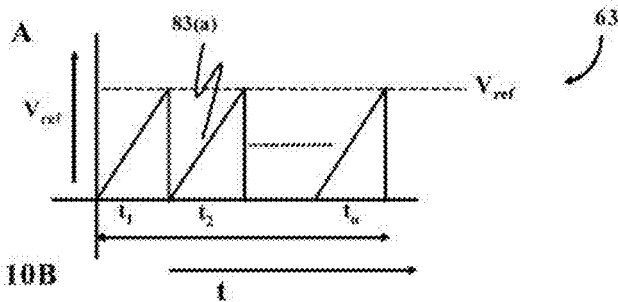
FIG. 11A is a schematic representing a filter circuit unit, a part of signal post processing, according to this invention.
Figure 11A:
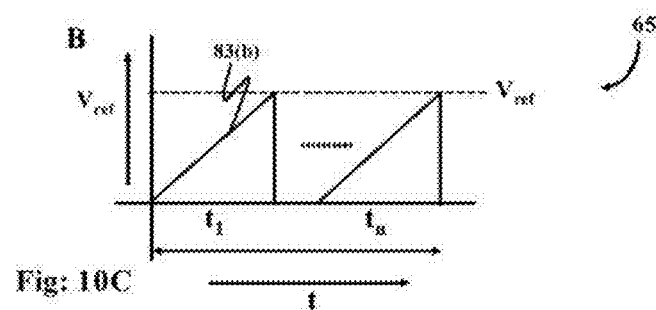
Figure 11A:
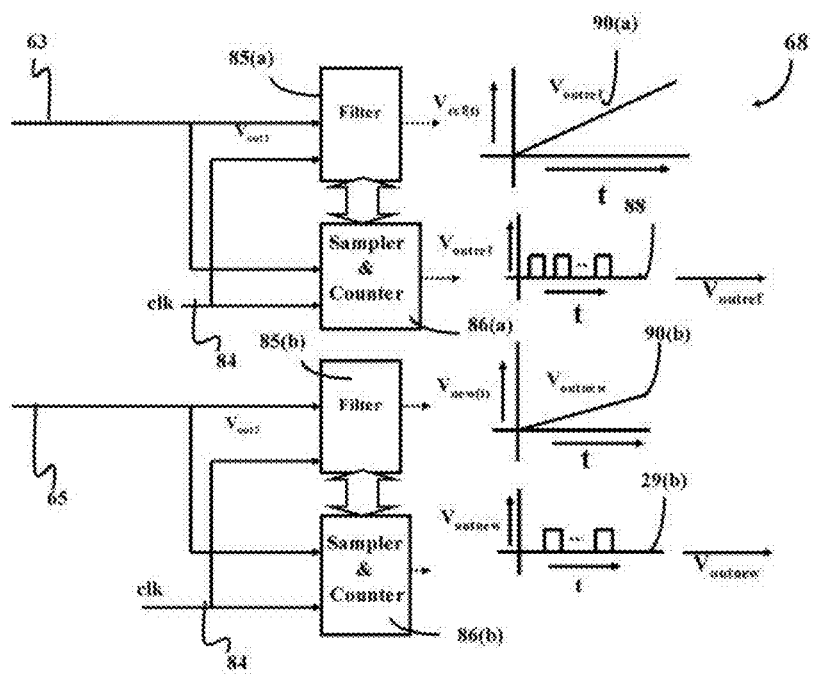

FIG. 11A is an example of the schematic showing the Filter-circuit of processing circuits 28 blocks shown in FIG. 9, according to this invention wherein the similar numerals represent the same parts as shown in FIGS. 10A, 10B, and 10C. The filter & sample-counter means block 68 is a part of the electrical processing circuit 28 and comprises with an common clock signal 84, two sets of filters 85(a) and 85(b), and two sets of sample counters 86(a) and 86(b). Two sets are used to process the outputs 63 and 65 separately. The filter & sample-counter block 68 is used to convert the waveforms achieved from the reference value 63 (with no specimen present) and new value 65 (with specimen present). In FIG. 11A, "Filter" blocks 85(a) and (85(b) are used to avoid glitches of the signals generated from the integrated circuit, explained in FIG. 10A. The "Sampler & Counter" blocks 86(a) and 86(b) can be used to compare the values of "Filter" blocks 85(a) and 85(b) to the values from the integrated circuit 66, in FIG. 10A.

FIGS. 11B and 11C show the output signals 63 and 65 with capture time at different points for example at 87(a) and 87(b). These two signals 63 and 65 will provide us with two saw-tooth based waveforms with different slopes; represent the output signal amplitude (not shown here). They can have the different time intervals for example, $t_1, t_2, t_3$ - - - $t_n$, total of 'tn' for output signal 63 (no specimen absorption) and $t_1'$, $t_2'$, - - - $t_n'$, total of the same time 'tn' for output signal 65 (with specimen absorption) for analysis. Several techniques can be used to analyze the waveforms to detect the concentration of the specimen absorbed. According to this invention, certain capture point 87(a) and 87(b) in waveforms 63 and 65, respectively, can be used at different intervals and different amplitude to avoid the noise, if any, presence in the signals. The output signals from sampler and counter circuits 86(a) and 86(b) after capturing can be the stream of the digital signals 88 as shown FIGS. 11B, and 88 and 29(b) as shown in FIG. 11A. The corresponding analog signals output from filter circuits 85(a) and 85(b) is an integrated signals 90(a) and 90(b), respectively.

Figure 12:
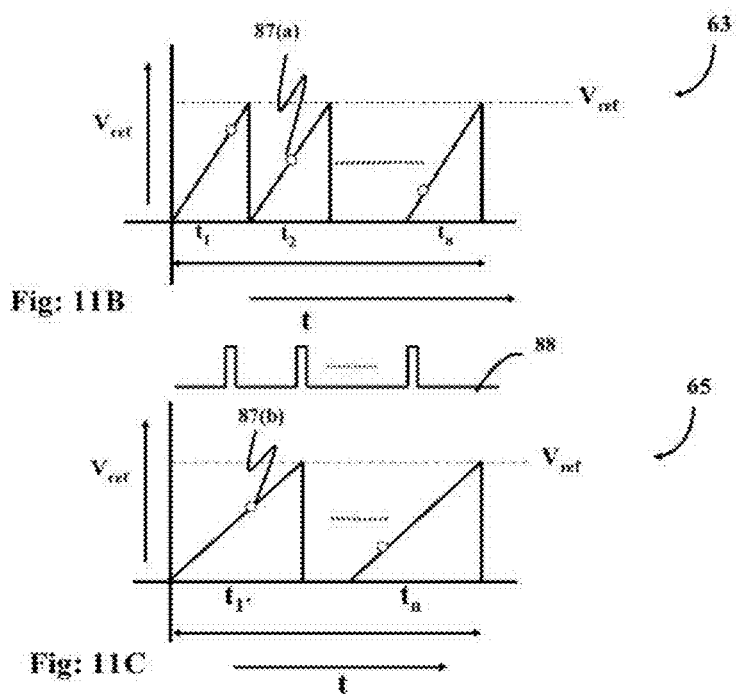
FIG. 12 is a schematic representing a read-out circuit used to store the reference signal.
Figure 12:
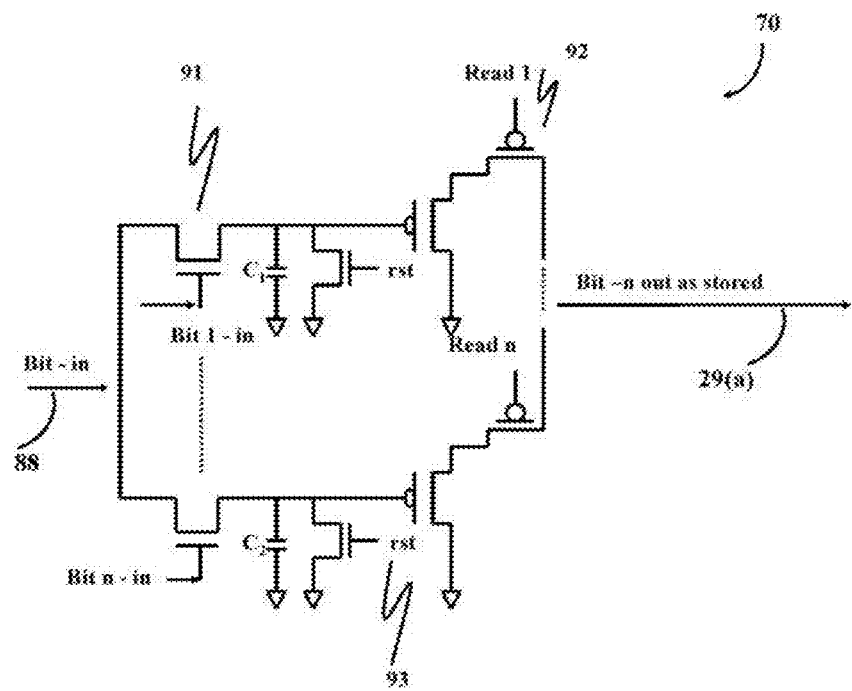
Figure 13:
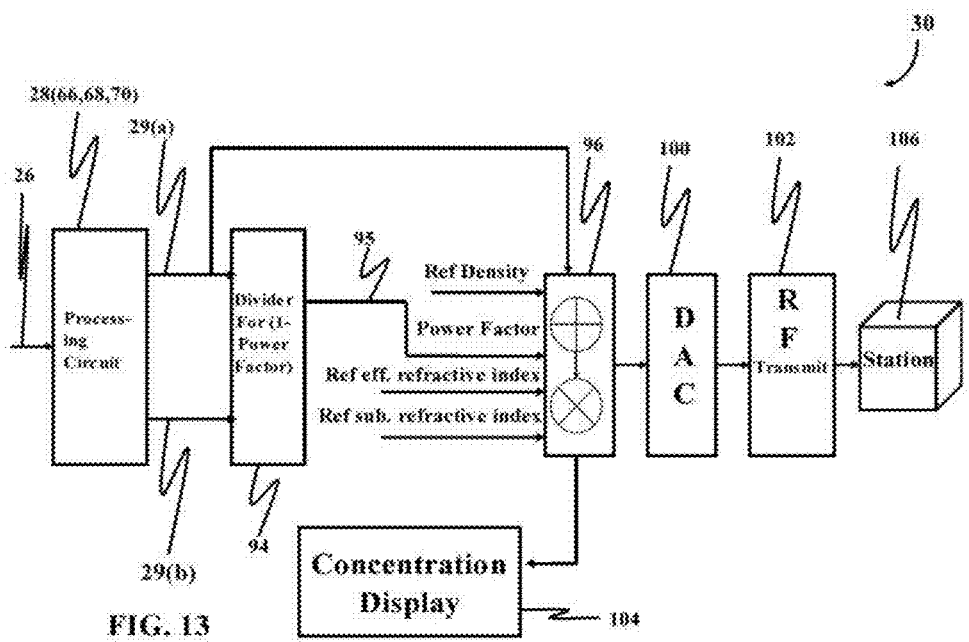
FIG. 13 is a block diagrams representing monitoring unit according to this invention.

FIG. 12 is the schematic showing an example of read-out circuit, a part of processing circuits 28 blocks shown in FIG. 9, according to this invention wherein the similar numerals represent the same parts as shown in FIGS. 10A and 11A. The read-out circuit means 70 shown in FIG. 12 averages the waveforms and then stores in the memory. Signals 88 received for reference value, will be stored into a read-out circuit 70, shown in FIG. 12, which is a part of the electrical processing circuit 28, as shown in FIG. 9. Read-out circuit 70 could be one for each of the reference value or specimen value to store (not shown here). Alternatively, one read-out circuit for reference value store can also be used which is used in FIG. 9 as for example. Any number of bits can be used for read-out circuit. As for example, a 12-bit circuit is considered in FIG. 12. This read-out circuit 70 can be fabricated utilizing standard CMOS process technology. For example, this read-out circuit can be fabricating with standard 350 nm, 3.3 volt, and thin-oxide digital CMOS process geometry or less. The data will come to each bit (1-12) 91 of pass-gate transistor for storage. After the data is stored in the transistor, read-out port 92 will give us the stored values as outputs 29(a) for the reference value 88. This circuit will have a 'reset' line 93, so that we can flush out the older data, if necessary. This circuit can be single transistor CMOS, p and n-channel transistor CMOS, or capacitive based circuit, which can be fabricated using conventional CMOS technology. FIG. 13 is the schematics showing the block diagrams of the monitoring system, according to the invention, wherein the same numerals represent the same parts, explained in FIGS. 9, 10A, 11A, and 12, so that repeated explanation is omitted here. This monitoring system 30 comprise of several blocks such as: "Divider for (1-Power Factor)" block 94, Digital Signal Processing (DSP) unit 96, Digital to Analog Conversion (DAC) block 100, Radio Frequency (RF) Transceiver block 102, Concentration Display block 104 and remote Station block 106 to monitor the analyzed value. The RF unit 102 is for remotely monitor the specimen.

The signals 29(a) and 29(b) from the processing circuit unit 28 feed to the divider circuit 94 to calculate (1-power factor), as shown in EQ. 9, and its resultant output signal 95 feeds to the n-bit digital signal-processing unit 96, where n is the number of the bit. Other inputs to DSP unit are known parameters such as reference concentration (mentioned as background concentration of the specimen, if any), other required refractive indices related to the nano-chips, explained earlier. The DSP unit 96 is commercially available from various vendors or the unit can be fabricated with standard CMOS technology, depending on the specification criterion. This DSP unit 96 includes a system controller for coordination. The system controller of the DSP unit 96 may be chosen to be an n-bit RISC/CISC-type processor, which is commercially available by various vendors such as Texas Instrument, INtel. The processor and system controller may share a memory for program and data storage.

Output signals of the DSP block 96, which are digital signals, can be converted into analog by using the "DAC" block 100. Output signals from the "DAC" block 100 can be transmitted through the "RF Transceiver" block 102. Signals from block 102 may be wirelessly monitored from the remote "Station" block 106 by using standard wireless protocol such as BLUETOOTH, 802.11a/b/g protocol or other proprietary protocols. The system can be embed with the standard (display) based monitoring unit 104 by feeding a part of DSP signal to the monitoring unit 104 to monitor in real time the concentration of the specimen.

According to this invention, whole processing unit can be made into a single chip and can be fabricated using standard IC technology. Alternatively, whole processing unit can be also build hybridly.

According to this invention, FIGS. 9 to 13 explain the signal-processing unit to monitor the specimen concentration. This is given for example only. Various signal processing ways (utilizing similar idea as shown in FIGS. 9-13) can be used to monitor the specimen concentration. For example, alternatively, single switch (single pole double through) can be used instead of using two switches (S1 and S2), explained in FIG. 10A. In addition, alternatively analog divider (not shown here) can also be used instead of using digital divider 94, (shown in FIG. 13). Additional analog to digital converter may require converting the resultant analog signal after dividing by divider (not shown here).

According to this current invention, any microprocessor, FPGA, or ASIC circuit can be used instead of DSP to perform the DSP functionality. These are available from the commercial vendors. For example, microprocessor can be obtained from Intel, FPGA from Actel and Xilinx, and ASIC circuit could be custom designed for required functionality, and it can be off-shore design and manufacturing.

According to this invention, alternatively the read-out memory circuit can be made based on capacitive load. FIG. 14 shows a schematic diagram of an alternative read-out circuit, wherein same numerals represent the same parts as shown in FIG. 12, so that repeated explanation is omitted here. The difference of read-out circuit as shown in FIG. 12 is that read-out circuit 118 in FIG. 14 is based on capacitive load 110 and a 1 to 1 switch 112. The advantages of using this circuit are: low area and low power. At least one 1 to 1 switch 112 and at least one capacitive load 110 can be used for single bit of memory. Input signal 88 can be stored by each capacitor 110 and the stored values can be as output signal 29(a) as a reference (initial) value.

According to this invention, the signal processing unit and the monitoring units both as shown in FIGS. 9 to 14 can be fabricated monolithically into a single chip. Standard Si-CMOS technology can be used for fabricating the signal processing and monitoring chip either in single chip form or multiple chips. The geometry of the silicon-CMOS technology can be ranged from 0.35 µm 20 nm or less. The divider 94 can be designed in different ways for example carry-save, Boolean, binary type or synthesis library specific type, depending on the desired performance and area.

FIG. 15 shows a schematic of the nano-sensing detection system unit according to this invention wherein the same numerals represent the same parts as explained in FIGS. 2 to 14, so that repeated explanation is omitted here. The sensing means 120 comprises with at least one laser 12 connecting with electrical driver 122 through electrical connection 124, splitter 126, nano-chip 16(a, b, c, d, e), at least one detector 20, signal processing unit 130, connecting with the external power supplies through connection 132, and a common carrier substrate 134. According to this invention, light 14 having fixed wavelength is made to couple to the 1×k splitter 126 (where k is the number of splitters which is at least one) to split the intesity of light 14 into k numbers and made to pass through the nano-sensor 16(a, b, c, d and e). Alternatively, according to this invention, the splitter and nano-chip can also be designed to operate in broadband light. In that case, the waveguide is to be multi-mode to operate in broad spectrum of light.

The splitter can be designed based on the photonics crystals having rod or holes, arranged periodically to made photonic band gap structure. Both splitter and nano-chips can have the same photonic band gap structure or different, and they can be fabricated on the common substrate 136. Alternatively, the splitter can be designed based on the homogeneous (solid) substrate (without photonics crystal) and the nano-chip can be based on photonic crystal base. Again, they can be fabricated onto the common substrate 136, or both splitter 126 and nanochip 16(a, b, c, d and e) can be fabricated in separate substrates, and afterwards hybridly packaged onto the common substrate (not shown here). To detect different types of specimens. For example different bio-molecules, different types of receptors can be used in the nanochips. The outputs from each nanochip are made to incident to the detector 20 to convert optical signal into corresponding electrical signals (not shown here). The electrical signal is processed by the IC 130 to determine the concentration of each specimen. The electrical IC 130 can be single chip or multiple chip based on the circuit means, as explained previously from FIGS. 9 to 14. All electrical components can be made into the single chip. Optical chip comprising with the splitter and the waveguide, and single chip can be packaged on the common substrate 134 to make the small package of dimension below 1"×1"×0.5" (W×L×H). A key feature of this system 120 is that multiple sensors can be fabricated on a single wafer 136. Utilizing the multiple sensor help to detect multiple specimens at the same time. For example, one sensor can detect chemical agent sensor, the second can be a biomolecule sensor, and the third can be a biological cell detector, and so on. Other example could be a single sensor unit can detect different gases or different types of bio-molecules simultaneously in real time, and any combination thereof.

FIG. 16 is a schematic representing the small form-factor sensor system, according to this invention, wherein the same numerals represent the same parts, as explained in FIGS. 2 to 7 and 15, so that repeated explanation is omitted here. The small form factor sensor system 138 comprises with two parts wherein first part is a passive section of the system and comprises with sample handler 140, two waveguides 142(a) and 142(b) for incoming and outgoing optical signals 14 and 18, respectively, and a common substrate 144, and the second part is an active section of the system and it comprises with carrier substrate 146, laser 12, laser driver 122, detector 20, preamplifier 148, signal processing integrator circuit 150, and electrical connection 152.

According to this invention, specimen 154(a) is made to pass through the inlet 156(a) of the specimen handler 140 and pass out the specimen 154(b) from the outlet 156(b). The passive section of the sensor system 138 is designed in a way that a portion of its internal section is made to expose to the nanochip 16 to make enough contact of the specimen while passing through this specimen handler 140. The optical signal 14 is made to propagate through the nanochip 16 via waveguides 142(a) and 142(b) used for guiding the signals on the passive section of nano-chip 16. For simplicity in handling and also for the purpose of reusage of the sensor system for long time, the passive section can be a separate section apart from the active section, and can be replaceable and easily stackable to the active section. Alternatively, both passive and active sections could be single section attached permanently. In FIG. 16, an example of a small form-factor sensor system containing a single nano-chip 16 is shown for simplicity in drawing. This can cover also for m-number of sensors containing in passive section of the sensor system (not shown here) for m-number of specimens detection. In that case, at least one specimen handler can be used and each nano-chip can have with same or different receptors.

According to this invention, the active section of the sensor system 138 has signal transmitting section, OE (optical to electrical conversion), and signal processing units (not shown separately). Transmitting section comprises with the laser 12 and driver 122, OE unit comprises with detector 20 and preamplifier 148, and signal processing unit comprising with a chip 150 for further signal processing and monitoring. The signal processing chip 150 contains pre-processing unit, post processing, and monitoring units, explained earlier in FIGS. 9 to 14. Transmitting, OE, and signal processing units are placed on the carrier substrate 146 and they can be hybridly integrated on carrier substrate 146 or fabricated monolithically as single chip. The carrier substrate 146 has the groove 158, housed appropriate to the passive section holding. Under operation, both waveguides 142(a) and 142(b) are coupled to the laser 12 and detector 20, respectively to transmit and receive the signals 14 and 18 to and away from the nano-chip. Source (e.g. laser diode or light emitting diode) 12 with specific wavelength or ranges of wavelength, appropriate to the refractive index of the nano-chip 16 can be used and it can be electrically driven by the driver circuit 122. The OE section has the detector 20, having high sensitivity to the source light, can be used to convert the optical signal to electrical. The detector signal is amplified by the pre-amplifier 148 and processed by the chip 150 for post processing and monitoring the concentration of the specimen. The electrical connection 152 connects all electrical components to the external power supplies (not shown here). According to this invention, transmitter section, OE section, and signal processing section can be fabricated into a single chip utilizing the standard IC technology. Alternatively, each component in active section could be a separate component, hybridly integrated on the substrate (e.g. 146).

According to this invention, the nano-chip described from FIGS. 3 to 7 and FIGS. 14 and 15, can be fabricated using any kind of substrates which cover, semiconductor, polymer, ceramic, exhibiting optical properties. Semiconductor cover Si, III-V or II-VI based compound semiconductors. The rods or holes, periodically arranged inside substrate and/or in waveguide to form the photonic crystal structure, can be made by utilizing standard wet or dry-etching process frequently using in IC manufacturing. Alternatively, electrochemical or photo-electro-chemical etching process can also be used to create the holes inside the substrate. According to this, alternatively air-spheres inside can also be used forming photonic crystal based nano-chip, and they can be made by conventional electrochemical process. For example, large scale of air-spheres in silicon, strong variation of the diameter with a length of the lattice constant can be made using photo-electro-chemical process for crating photonic crystal structure for the nanochip. Alternatively, porous material (semiconductor, insulator, polymer, or metal) having pores can also be used for fabricating nanochip. The waveguide and the substrate carrying the waveguide could be same kind of material or different material. Alternatively, nanochip can also be made from the combination of the nanoparticles deposited or synthesized on the substrate arranged in periodically.

Alternatively, according to this invention, the nanometer sized rods, wire or tubes can also be made from the carbon type materials (semiconductor, insulators, or metal like performances) such as carbon nano-tubes, which could be single, or multiple layered. They can be made using standard growth process for example, MOCVD, MBE, or standard epitaxial growth. According to this invention, the self-assembled process can also be used to make wires, rods, or tubes and their related pn-junction to increase the junction area. These tubes can be grown on the semiconductors (under same group or others), polymers, or insulator. Alternatively, according to this invention, these rods, wire, or tubes, can be transferred to the foreign substrate or to the layer of foreign substrate acting as a common substrate for waveguide for nano-chip. The foreign substrate or the layer of material can be any semiconductor such as Si, Ge, InP, GaAs, GaN, ZnS, CdTe, CdS, ZnCdTe, HgCdTe, etc. The substrate can cover also all kinds of polymers or ceramics such as AlN, Silicon-oxide etc. The material can be conductive or non-conductive.

According to this invention, different substrates can be used for making sensing device as shown in FIGS. 14 and 15. For example, carrier substrate 134 and common substrate 136 for the splitter and nanochip can be same or both can be different substrate, in hybrid integrated together. Alternatively, the splitter used for the multiple nanochip can be fabricated from the separate substrate and integrated on the carrier substrate 134. As a carrier substrate, substrate made of any kind of material such as semiconductor, ceramic, metal, or polymer can be used.

Figure 17:
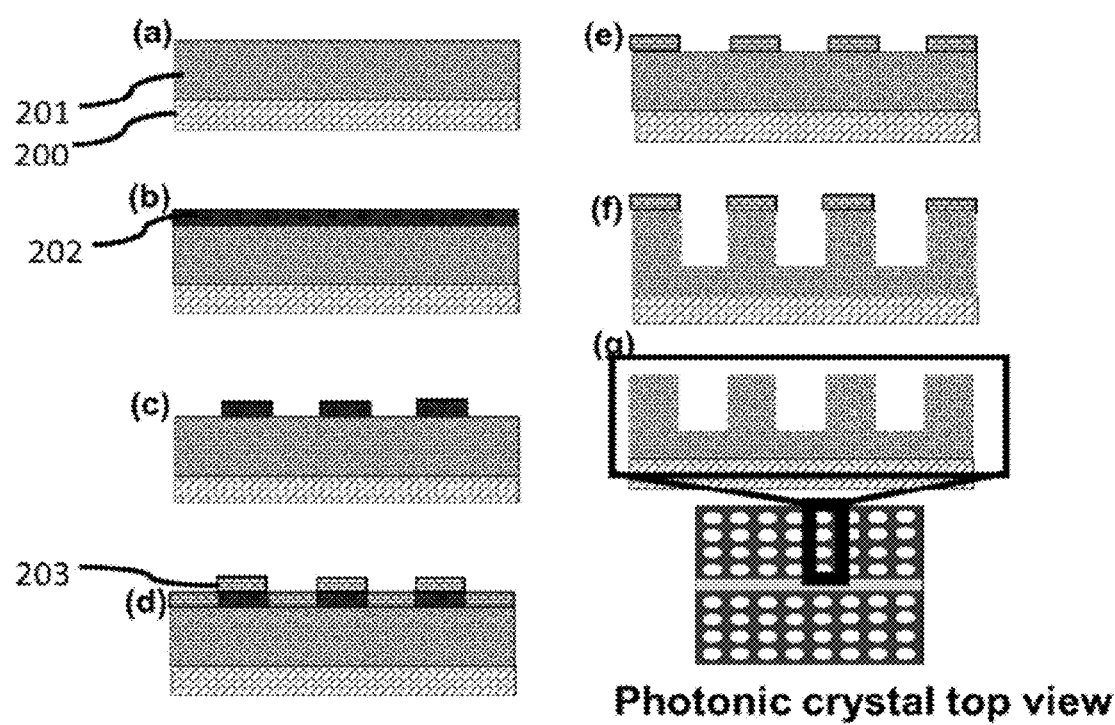
FIG. 17 is a schematic showing the manufacturing process for the nanochip, according to this invention.

According to this invention, concentration measurement by determining the power factor is explained here. This nanochip based on photonics crystal can also detect the concentration by other methods, such as measuring the fringe-pattern by using of CCD camera and laser beam analyzer, or absorption spectrum of the optical output by spectroscopy. The concentration and type of the specimen can be known by comparing with the reference pattern for the case fringe pattern technique, and by comparing intensity and chemical absorption for the case of absorption spectrum technique. Turning now to FIG. 17a-g, the chip made from photonic crystal (PC) structure (herein after mentioned as photonic crystal coupled waveguide as "PC-W") can be fabricated in a number of ways. For example, this description will use Silicon Nitride (SiNx) based photonic crystal structures which have a refractive index of 1.5-2.0. FIG. 17 summarizes the procedure for preparing SiNx PC-W structure. A fused silica substrate 200 may be used as the common substrate to integrate multiple PC-W sensors. In FIG. 17a, the functional SiNx material 201 is deposited either using PECVD or LPCVD. In FIG. 17b, photoresist layer 202 is deposited on the SiNx. In FIG. 17c, photoresist layer 202 is lithographically patterned followed by, in FIG. 17d, the deposition of a thin layer of chrome 203 to serve as a mask for subsequent pattern transfer of the PC-W holes. With the residual photoresist removed via acetone liftoff, in FIG. 17e, Cr mask on the remaining surface defines the areas that are to be etched in SiNx layer using anisotropic $NF_3$ dry etch, as shown in FIG. 17f. The remaining chrome layer is then removed in FIG. 17g. The structure shown in FIGS. 17a-g are intended to show a cross-sectional view of the chip made from photonic crystal structure for bio-agents diagnosis.

The materials discussed above are, however, merely an example. Other material systems can also be used, for example, when desiring formation of a disposable test strip. In such a case, microfluidics based blood plasma filtration unit coupled with PC-W sensing platform may be provided as disposable plastic test strips. To keep the material and fabrication cost down for fabricating plastic based PC-W sensors and blood plasma filtration unit in a single microfluidic channel, replica molding procedure provides a low-cost alternative.

In addition to the PC-W structural design, surface treatment to covalently conjugate bioreceptors is a part of the sensor design and optimization. The key parameters of surface treatments that influence the biosensor performance include the orientation and surface coverage of the conjugated bioreceptors. Due to the glass-like surfaces of the SiNx and fused silica all-dielectric photonic crystal, typical surface treatment techniques from biochemistry such as chemical etching techniques, vapor or plasma deposition, and the formation of self-assembled monolayers (SAMs) can be utilized for immobilizing bioreceptor layer.

Silicon Nitride (SiNx) structure surface can be modified by using one of the two SAM organosilanes, i.e. 3-(2-aminoethylamino) propyltrimethoxysilane (for $NH_2$ grafting), or 10-(Carbomethoxy)decyl dimethylchlorosilane (for COOH grafting after activation with HCl). To perform the $NH_2$ silanisation the samples need to be placed in a solution containing methanol and acetic acid glacial, eventually adding the $C_8H_{22}N_2O_3Si$. For COOH grafting, the samples need to be immersed in a solution of $C_{14}H_{29}ClO_2Si$ dissolved in a mixture of $CCl_4$ and $n-C_7H_{16}$ followed by final immersion of the samples in HCl solution. After successful silanization of the surface, the bioreceptors may be selectively immobilized through diffusion onto the sensor surface by placing several small drops of bioreceptors directly above the respective PC-W sensor units. The samples then need to be incubated and thoroughly cleaned to remove any unbounded bioreceptors onto the surface. To passivate the sensor surface from non-specific biomolecule binding, detergent blockers such as Tween-20, Triton X-100 or protein blockers such as Bovine serum albumin (BSA) may be used.

Figure 18:
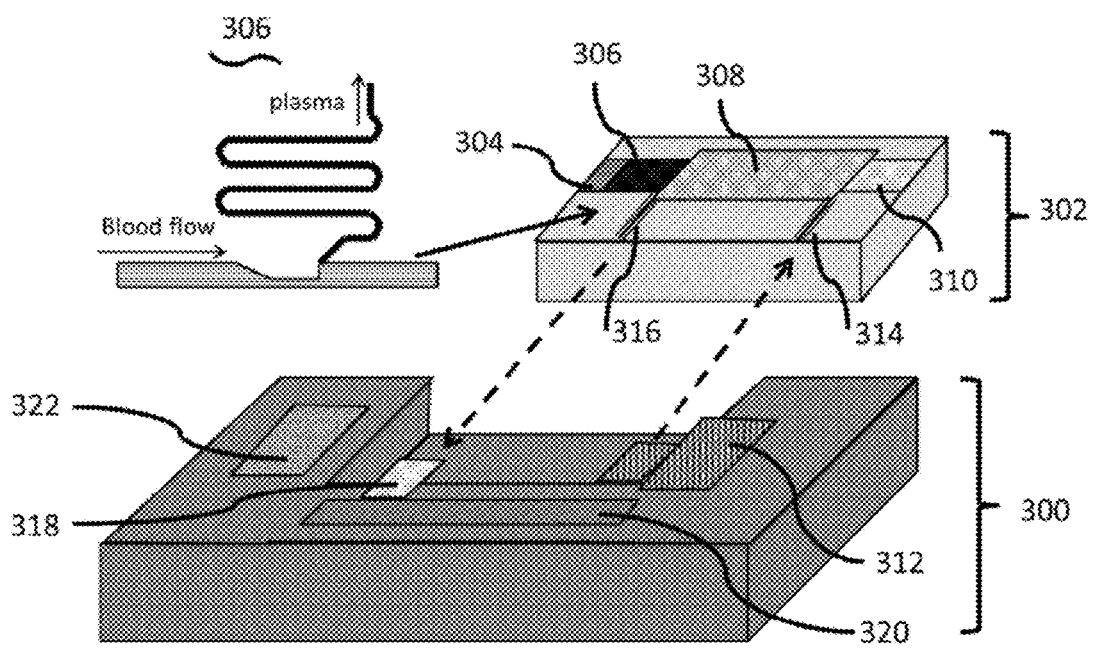
FIG. 18 is a schematic showing an embodiment including a blood filtration system on a disposable test strip, which is connectable to the diagnosis device, according to this invention.

While it has previously already been mentioned that the above embodiments can be used to identify any number of biomolecules, a few specific applications are also beneficial. Specifically, an embodiment for sensing pathogens (such as Hepatitis B) or HIV can be created. FIG. 18 shows one such preferred embodiment, according to this invention. As shown in the FIG. 18, when using the present invention to test for specific molecules within the human body, some additions and modifications to the structure are favorable. FIG. 18 shows, for example, where a portion of the device, 302, is removable from the main body 300. Here, a blood sample enters the inlet 304 on the test strip 302, passes through a blood filtration system 306, the PC-W sensing platform 308, and then exits the strip through outlet 310. The laser and laser source 312 are placed on the main body 300 in such a way as to direct the laser into waveguide 314 located on the test strip 302. The laser signal then travels through the PC-W sensing platform 308, exits out of waveguide 316, and is sensed by the detector 318 on the main body of the device. The integrated circuit 320 converts the laser signal to an electrical signal, analyzes it, and displays the result in the display screen 322. Connections between the various components are not shown in FIG. 18.

FIG. 18 shows an additional component from those embodiments discussed previously (such as that shown in FIG. 16), known as a blood filtration system 306. During measurement, a small volume of blood sample (e.g at least a drop) needs to be flow into the microfluidic channel (not shown). The microfluidic channel will include a filtration chip for extracting plasma from the whole blood sample. The filtration chip comprises microfluidic channels that use hydrodynamic forces to separate human plasma from blood cells. Individual filtration unit (not shown here as part of the blood filteration unit 306) comprises an inlet that is reduced by approximately 20 times to a small constrictor channel. This channel opens out to a larger output channel with a relatively small lateral channel for the collection of plasma. Studies have shown that this type of filtration unit was capable of removing 97.05±0.5 percentages of cells at 200 $\mu l\ min^{-1}$ flowrate. The plasma from the filtration chip flows onto the PC-W sensing units through a dedicated channel allowing the target biomolecules to bind to the bioreceptors. Before the optical measurement, a stringent cleaning procedure using a buffer solution may be used to eliminate non-specific biomolecule interactions since they can negatively influence the output optical signal. The two waveguides, 314 and 316, attached to the test strip facilitate the transport of the optical signals from the laser source to the PC-W sensing arrays and from there into the signal processing unit for data analysis. A small display unit 322 will be included for displaying the test results real-time. The integrated point-of-care diagnostic platform can be powered by conventional Li-ion batteries.

Figure 19:
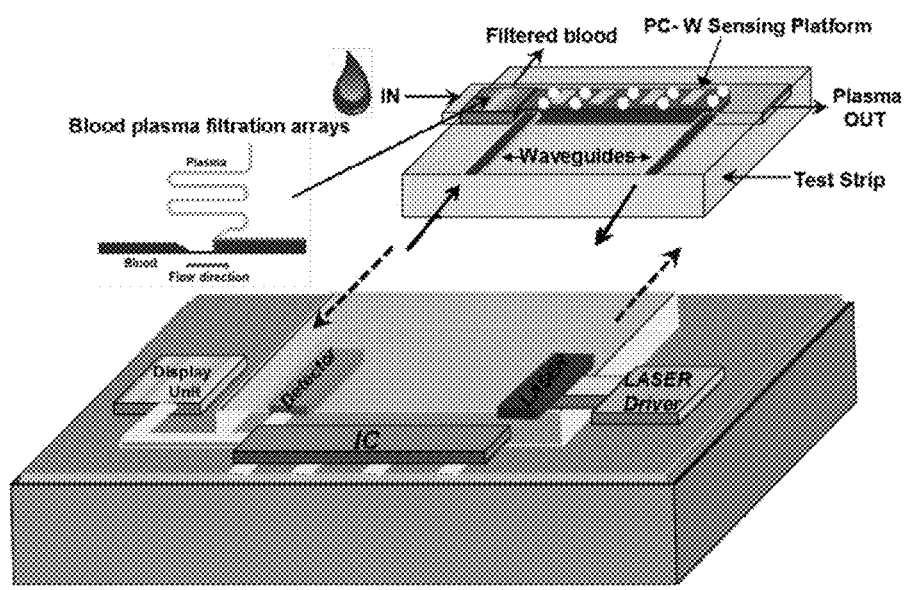
FIG. 19 is a detailed illustration of a potential embodiment, based on the schematic shown in FIG. 18, according to this invention

FIG. 19 in included as an example of a more detailed diagram from the generalized FIG. 18, according to this invention. It is included merely as an additional aid to visualize possible embodiments, and is not intended to be limiting the present invention.

Pathogen-Sensing

The embodiment may be designed to have arrays of independent biosensing units coupled onto the PC-W platform, providing parallel detection of multiple biomarkers. While this is beneficial for all types of detection, this is especially beneficial when detecting certain pathogens, such as HBV, which have multiple detectable markers. Numerous HBV markers include hepatitis B surface antigen (HBsAg), hepatitis B surface antibody (anti-HBs), hepatitis B e antigen (HBeAg), hepatitis B e antibody (anti-HBe), hepatitis B core antigen (HBcAg), and hepatitis B core antibody (anti-HBc). For maximum accuracy, test strips may be designed to detect approximately five different HBV markers.

Although this embodiment specifically utilizes a blood filtration system, alternatively the embodiment might be designed to detect biomarkers in saliva, other body tissue, or other body fluid. If this is the case, then the blood filtration system may be omitted or replaced with a different type of filtration system. For example, due to the viscosity of saliva, movement through a simple sample inlet may be difficult. A microfluidic system may be used to aid the movement of the sample into the PC-W sensor platform, wherein a drop of fluid may able to flow by capillary force.

HIV-Sensing

Another alternate embodiment is one which is designed to detect HIV. The typical HIV diagnosis tests are based on the detection of antibodies produced by the human body in response to the HIV infection. For clinical laboratory-based HIV screenings, enzyme-linked immunosorbent assay (ELISA) is the first test conducted to look for HIV antibodies. If the test indicates the presence of HIV antibodies (positive), the test is again repeated to confirm the diagnosis. In the case of second positive ELISA result, a complementary test called Western blot is deemed necessary to confirm the diagnosis since it is more adept at distinguishing HIV antibodies from other antibodies present in the blood. The need for advanced technical skills and higher operating costs limits the use of Western Blot only to a confirmatory test. Although assay based techniques such as ELISA and Western Blot provide diagnostic results with high accuracy, their major shortcoming is the high number of false negative diagnostic results during the "window period. The 3-12 weeks period between the onset of HIV infection and the appearance of measurable antibodies to HIV seroconversion is known as the window period. Among high-risk populations, the current antibody tests are shown to miss about 10 percent of acute HIV infections by showing antibody-negative. Alternate HIV testing methodologies involve the detection of HIV antigen, or nucleic acid amplification testing (NAAT). Antigen testing looks for soluble p24 antigen, presumably following viral replication, and does not specifically identify live virus. The level of p24 antigen increases significantly during the initial phases of the infection, then declines to undetectable levels as they bind to HIV antibodies [Christine C. Ginocchio, HIV-1 Viral Load Testing Methods and Clinical Applications, laboratory medicine (2001), 32 (3), 142-152]. Since the estimated average time from detection of antigen to detection of HIV antibodies is 6 days and not all recently infected persons have detectable levels of p24 antigen, HIV diagnosis using stand alone p24 antigen test is strongly discouraged, nucleic acid amplification testing (NAAT) procedure widely used for screening donated blood detects one or more of several target sequences located in specific HIV genes and can provide diagnosis much earlier than the antibody test. However, the drawbacks to NAAT testing include: need for sophisticated instrumentation, high operating costs and unaffordable in remote and non-laboratory settings. Therefore, there is still a strong need to develop a cost effective, laboratory-free diagnostic system that can detect acute HIV-1 in-house or in-remote settings of developing countries without the need for trained technicians or advanced facilities.

As described above, currently, HIV diagnosis in general is costly, and additionally inaccurate during the initial window after infection, and most importantly takes long time to get diagnosis results.

According to this invention, this embodiment is a diagnostic system that can diagnose HIV infection within the window period based on parallel detection of two characteristic HIV-1 biomarkers, i.e. HIV-1 Tat protein and HIV-1 antibodies (here in referred as antibodies). Tat protein is a primary HIV gene that regulates the early stage replication of HIV, whereas antibodies are produced by the body in order to combat the assortment of proteins produced by HIV infection. Bioreceptors are biomolecules attached to the transducer surface based on their high specificity towards target specimen to form a functional sensor. According to this invention, bioreceptors are used for TAT protein detection which provide the information on even before window period condition of the patient.

The multi-analyte diagnostic platform is based on biosensing device platform, as described previously in FIGS. 3 to 7 and also FIGS. 15, 16, 18, and 19 for measuring the miniscule refractive index changes when the biomarkers in the sample bind to the characteristic bioreceptors. The integration of blood plasma separation, optical biosensing and data processing assembly on the same platform makes possible the development of a sample-to-answer system with automated data analysis providing a rapid diagnostic readout (<30 min). In addition, the use of robust bioreceptors that have high storage stability at ambient conditions offers the potential to use the proposed diagnostic system in remote settings without cold storage facilities.

Structurally, the embodiment for detecting HIV may be very similar to that of the embodiment for detecting pathogens. It may utilize the same disposable plastic test strips and blood filtration system, and the only significant difference would be the biomarkers used in the photonic crystal arrays.

Figure 20A:
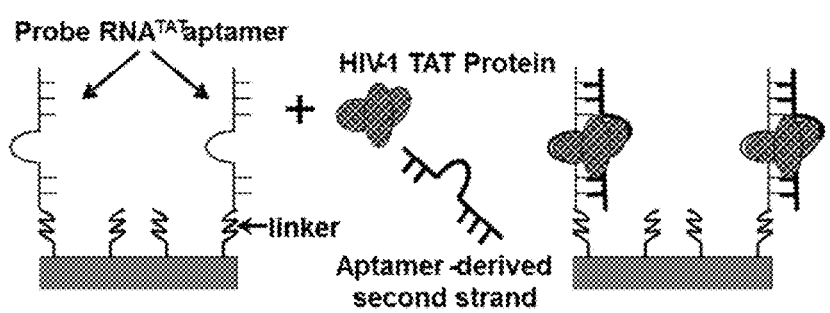
FIG. 20A is a schematic showing a illustrative diagram of the functionality of HIV-1 $RNA^{TAT}$ aptamers as bioreceptors for HIV-1 TAT protein binding and can be used in this biosensor, for diagnosis of HIV, according to this invention.

Detection of HIV can be done through detection of two indicators: HIV-1 Tat proteins or HIV-1 antibodies. For the detection of Tat protein, as shown in FIG. 20A, one may use an aptamer that binds to the Tat protein with two orders of magnitude greater (133-fold) affinity over the TAR RNA of HIV-1. Recently developed two aptamers: Probe aptamers-RNA$^{Tat}$ and aptarner-derived second strand (5'-UCGGUC-GAUCGCUUCAUAA-3'-NH$_2$ (SEQ ID NO:1) and 5'-GAAGCUUGAUCCCGAA-3' (SEQ ID NO:2) respectively) (available from Sigma-Aldrich Co) may be used to function as bioreceptors for the detection of real HIV-1 Tat protein extracted from blood. At first, the probe RNA$^{Tat}$ aptamers are covalently attached to the photonic crystal surface of the PC-W sensing platform. Once exposed to a blood sample, any present HIV-1 TAT proteins bind to the probe aptamers along with aptamer-derived second strands, thereby forming duplex structures. The high storage stability of aptamers even at ambient conditions can be used to develop diagnostic systems that do not require refrigeration to maintain their detection performance. Alternatively, a simple annealing step at 70° C. for 3 min may be used to recover the functional activity of immobilized aptamers up to 90%.

Figure 20B:
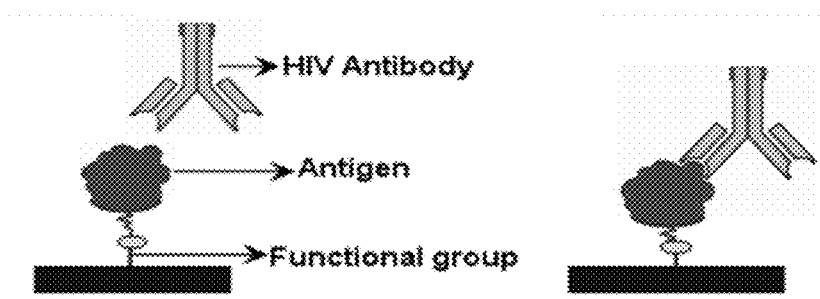
FIG. 20B is a schematic showing a Illustrative diagram of the functionality of HIV-1 antigens as bioreceptors for binding with antibodies for HIV diagnosis

Alternately, on the other hand, for the detection of HIV-1 antibodies, HIV proteins called antigens, shown in FIG. 20B, may be used as bioreceptors. The antigens are covalently attached to the biochips sensing platform (as described previously). Once exposed to a blood sample, any present HIV-1 antibodies bind to the antigens.

For maximum accuracy in testing, the embodiment may be designed, similarly to the HBV detector, with multiple independent parallel biosensing units, wherein each unit detects a different biomarker.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments is not intended to limit their scope. Although the invention has been described with respect to specific embodiment for complete and clear disclosure, the appended claims are not to be thus limited but are to be construed as embodying all modification and alternative constructions that may be occurred to one skilled in the art which fairly fall within the basic teaching here is set forth.

The present invention is expected to be found practically use in the industrial, commercial, and bio-medical application. Using of such sensor device will help to detect very low level concentration (in ppb level) of gases, requiring in industrial application. This sensor devices is not limited to use in chemical gas, bio-molecule gas only, this can also be used in biological cell detection and their low level concentration measurement. The main advantages of this invention are that detection and concentration of multiple specimens at a real time can be possible. Multiple specimens can be multiple gases, multiple bio-molecules, or multiple biological cells, or their combinations.

What is claimed is:

1. A sensing device comprising:
   a nanochip having a waveguide with a core and a cladding,
      said cladding having a periodic dielectric system that forms a photonic bandgap;
   a light source that sends optical signals through the core of said waveguide;
   a plurality of receptors for interacting with a specimen to be sensed, said receptors disposed in the periodic dielectric system of the cladding;
   a detector for converting optical signals sent through the core of the waveguide into electrical signals;
   at least one electrical processing circuit for processing electrical signals received from the detector, wherein said electrical processing circuit outputs a first signal and a second signal, wherein the first signal corresponds to the intensity of the optical signal passing through the waveguide without a specimen interaction with the receptors, and the second signal corresponds to the intensity of an optical signal passing through the waveguide with specimen interaction with the receptors;
   at least one monitoring system for determining concentration of a specimen based on signals received from the electrical processing circuit, wherein said monitoring system calculates a ratio of the first signal and the second signal, correlate said ratio to a change in effective refractive index of the cladding resulting from specimen interaction with the receptors, and correlate the change in effective refractive index to the concentration of the specimen; and
   at least one display unit.

2. The sensing device of claim 1, further comprising a plurality of nanochips, and a plurality of detectors, wherein each said nanochip utilizes a different type of receptors.

3. A sensing device comprising:
   a removable section, wherein said removable section comprising:
   a nanochip having a first waveguide with a core and a cladding, said cladding having a periodic dielectric system that forms a photonic bandgap;
   an inlet for specimens;
   a microfluidic system for allowing specimen to move from said inlet to said nanochip;
   an outlet for specimens; and
   a plurality of receptors for interacting with a specimen to be sensed, said receptors disposed in the periodic dielectric system of the cladding;
   a main body, wherein said main body comprising:
   a substrate;
   a light source;
   a detector for converting optical signals into electrical signals;
   at least one electrical processing circuit for processing electrical signals received from the detector, wherein said electrical processing circuit outputs a first signal and a second signal, wherein the first signal corresponds to the intensity of the optical signal passing through the waveguide without a specimen interaction with the receptors, and the second signal corresponds to the intensity of an optical signal passing through the first waveguide with specimen interaction with the receptors;
   at least one monitoring system for determining the concentration of a specimen based on signals received from the electrical processing circuit, wherein said monitoring system calculates a ratio of the first signal and the second signal, correlate said ratio to a change in effective refractive index of the cladding resulting from specimen interaction with the receptors, and correlate the change in effective refractive index to the concentration of the specimen; at least one display unit;
   a second waveguide for guiding optical signals from said light source to said nanochip; and
   a third waveguide for guiding optical signals from said nanochip to said detector.

4. The sensing device of claim 3, wherein said plurality of receptors are chosen for binding with HBsAg, anti-HBs, HBeAg, anti-HBe, HBcAg, anti-HBc, or a combination thereof.

5. The sensing device of claim 3 comprising a plurality of nanochips, and a plurality of detectors, wherein each said nanochip utilizes a different type of receptors.

6. The sensing device of claim 3, wherein the electrical processing circuit comprises: an electrical signal integration circuit for integrating electrical signals received from the detector over time; a filter and sample-counter circuit for removing electrical noise from the signals received from the electrical signal integration circuit and generating corresponding digital signals; and a read out circuit for storing digital signals received from the filter and sample-counter circuit.

7. The sensing device of claim 6, wherein the electrical signal integration circuit comprises: a transimpedance amplifier (TIA); a first switch and a second switch; an analog memory; a first integrator circuit and a second integrator circuit; a first comparator and a second comparator; and a differentiator, wherein: the TIA feeds through the first switch, through the analog memory, to the first integrator circuit; the first integrator circuit feeds to the first comparator, which is reset back to the first integrator circuit; the first comparator feeds into the monitoring system; the TIA feeds through the second switch to the differentiator; the analog memory feeds to the differentiator; the differentiator feeds to the second integrator circuit; the second integrator circuit feeds to the second comparator, which is reset back to the second integrator circuit; and the second comparator feeds to said monitoring system.

8. The sensing device of claim 6, wherein the filter and sample-counter circuit comprises: a common clock for generating a clock signal; a first filter for filtering signals received from the first comparator; a second filter for filtering signals received from the second comparator; a first sample counter for comparing signals received from the first comparator to signals received from the first filter; and a second sample counter for comparing signals received from the second comparator to signals received from the second filter.

9. The sensing device of claim 3, wherein the monitoring system comprises: a digital divider circuit for calculating said ratio; and an n-bit digital signal processing (DSP) unit for determining concentration of the specimen based on said ratio.

10. The sensing device of claim 3, further comprising a preamplifier for amplifying signals received from the detector.

* * * * *